(12) United States Patent
O'Sullivan et al.

(10) Patent No.: US 11,845,846 B2
(45) Date of Patent: Dec. 19, 2023

(54) FORMULATION FOR 3D PRINTING AND A 3D PRINTED ARTICLE

(71) Applicant: University of Limerick, Limerick (IE)

(72) Inventors: Kevin Jeremiah O'Sullivan, Limerick (IE); Leonard William O'Sullivan, Limerick (IE); Seamus Clifford, Limerick (IE); Alice Shannon, Limerick (IE)

(73) Assignee: UNIVERSITY OF LIMERICK, Limerick (IE)

( * ) Notice: Subject to any disclaimer, the term of this patent is extended or adjusted under 35 U.S.C. 154(b) by 597 days.

(21) Appl. No.: 16/642,205

(22) PCT Filed: Sep. 4, 2018

(86) PCT No.: PCT/EP2018/073748
§ 371 (c)(1),
(2) Date: Feb. 26, 2020

(87) PCT Pub. No.: WO2019/043253
PCT Pub. Date: Mar. 7, 2019

(65) Prior Publication Data
US 2020/0354542 A1 Nov. 12, 2020

(30) Foreign Application Priority Data

Sep. 4, 2017 (GB) ..................................... 1714169

(51) Int. Cl.
*C08K 3/22* (2006.01)
*B33Y 10/00* (2015.01)
(Continued)

(52) U.S. Cl.
CPC .............. *C08K 3/22* (2013.01); *A61B 6/583* (2013.01); *A61L 31/028* (2013.01); *A61L 31/18* (2013.01);
(Continued)

(58) Field of Classification Search
None
See application file for complete search history.

(56) References Cited

U.S. PATENT DOCUMENTS

| 2010/0041789 A1* | 2/2010 | Neffgen | B82Y 5/00 |
| | | | 523/117 |
| 2011/0264080 A1* | 10/2011 | Lim | B29C 70/88 |
| | | | 523/105 |

(Continued)

FOREIGN PATENT DOCUMENTS

| CN | 106009591 A | 10/2016 |
| CN | 106349431 A | 1/2017 |

(Continued)

OTHER PUBLICATIONS

Hsin-Ta Wang et al., "In Vitro Biocompatibility, Radiopacity, and Physical Property Tests of Nano-Fe304 Incorporated Poly-l-lactide Bine Screws", Polymers, vol. 9, No. 12, May 26, 2017, p. 191.

(Continued)

*Primary Examiner* — Alexandre F Ferre
(74) *Attorney, Agent, or Firm* — FOX ROTHSCHILD LLP

(57) ABSTRACT

A flowable liquid formulation for 3D printing is described. The formulation comprises from 0.1 to 25 wt. % radiopaque particles, wherein at least 50% by weight of the particles have a diameter of at most 100 nm. The formulation further comprises monomeric, oligomeric and/or polymeric precursors adapted for polymerization to form a solidified article. Also described is an article (100) formed by 3D printing, the article (100) comprising a first 3D printed region (110) having a first radiopacity and a second 3D printed region (120) having a second radiopacity, wherein the first radiopacity is greater than the second radiopacity. Also described is a method of forming the article (100).

9 Claims, 13 Drawing Sheets

(51) Int. Cl.
  B33Y 80/00       (2015.01)
  B33Y 70/00       (2020.01)
  B29C 64/106      (2017.01)
  A61B 6/00        (2006.01)
  A61L 31/18       (2006.01)
  A61L 31/02       (2006.01)
  B33Y 70/10       (2020.01)
  B29K 509/02      (2006.01)
  B29L 31/00       (2006.01)

(52) U.S. Cl.
  CPC ............ *B29C 64/106* (2017.08); *B33Y 10/00* (2014.12); *B33Y 70/10* (2020.01); *B33Y 80/00* (2014.12); *B29K 2509/02* (2013.01); *B29K 2995/0011* (2013.01); *B29L 2031/753* (2013.01); *C08K 2003/2244* (2013.01); *C08K 2003/2286* (2013.01); *C08K 2201/003* (2013.01); *C08K 2201/011* (2013.01)

(56) References Cited

U.S. PATENT DOCUMENTS

| | | | |
|---|---|---|---|
| 2012/0065755 A1* | 3/2012 | Steingart | B33Y 30/00 700/98 |
| 2014/0099351 A1 | 4/2014 | Adams et al. | |
| 2015/0072293 A1* | 3/2015 | DeSimone | B33Y 30/00 355/18 |
| 2016/0009029 A1* | 1/2016 | Cohen | B29C 64/209 264/250 |
| 2016/0113846 A1 | 4/2016 | Willner et al. | |
| 2016/0175085 A1 | 6/2016 | Johnson et al. | |

FOREIGN PATENT DOCUMENTS

| | | | | |
|---|---|---|---|---|
| CN | 106747429 A | | 5/2017 | |
| EP | 1508834 A2 | | 2/2005 | |
| EP | 2990061 A1 | * | 3/2016 | ........... A61L 24/001 |
| EP | 3162469 A1 | | 5/2017 | |
| WO | 2006/116720 | | 11/2006 | |
| WO | 2007/056761 | | 5/2007 | |
| WO | 2012/064573 | | 5/2012 | |
| WO | 2014039825 A2 | | 3/2014 | |
| WO | 2014/138684 | | 9/2014 | |
| WO | WO-2015033093 A1 | * | 3/2015 | ........... A61K 31/404 |
| WO | 2015/165363 | | 11/2015 | |
| WO | 2016/019078 | | 2/2016 | |
| WO | 2016/168718 | | 10/2016 | |
| WO | 2016/176444 | | 11/2016 | |

OTHER PUBLICATIONS

Search Report dated Dec. 1, 2017 in GB Application No. 1714169.8.
Search Report dated Feb. 19, 2018 in GB Application No. 1714169.8.
International Search Report dated Apr. 10, 2019 in PCT/EP2018/073748.

* cited by examiner

600A

600B

FORMULATION FOR 3D PRINTING AND A 3D PRINTED ARTICLE

CROSS REFERENCE TO RELATED APPLICATIONS

This application is a § 371 national phase entry of International Patent Application No. PCT/EP2018/073748, filed Sep. 4, 2018, which claims priority to and the benefit of Great Britain Patent Application No. 1714169.8 filed on Sep. 4, 2017, both of which are hereby incorporated herein by reference in their entireties.

FIELD

The present invention relates to a formulation for 3D printing and a 3D printed article.

BACKGROUND TO THE INVENTION

Ionising radiation may be used in medical applications, for example medical diagnostics and medical therapeutics. For medical applications, ionising radiation includes gamma rays and X-rays. Medical imaging is a diagnostic medical application, typically using X-rays to create visual representations of interiors of bodies, for example human and/or animal bodies. For example, radiography uses X-rays to create two dimensional (2D) images. Fluoroscopy creates such 2D images in real-time and projectional radiography creates 2D persistent images using film or digital media. For example, tomography creates three dimensional (3D) images using 2D sectioning. X-ray computed tomography (CT), also known as Computed Axial Tomography (CAT), creates three dimensional (3D) images using 2D X-ray sectioning. Radiation oncology is a therapeutic medical application, typically using gamma rays and/or X-rays in treatment of cancer.

Medical imaging apparatuses typically require calibration, thereby providing image-to-image and/or apparatus-to-apparatus reproducibility. For example, X-ray apparatuses may be calibrated to compensate for performance of and/or variation of X-ray source, X-ray flux, X-ray flux distribution and/or X-ray detection. Calibration standards may be provided for this apparatus calibration. Additionally, and/or alternatively, medically-relevant calibration standards may be provided, for example, fracture samples for calibration and/or teaching purposes. Such medically-relevant calibration standards are typically provided from biological sources, thus giving rise to variations between nominally equivalent medically-relevant calibration standards.

Some medical devices, for example radiation oncology shields, selectively attenuate X-ray flux, to provide required therapies and/or reduce adverse effects. Provision of custom oncology radiation shields, for example for personalised patient therapy, may be costly and/or complex. Some medical devices, for example implantable biomedical devices, are implanted into the interiors of bodies by surgery. Inspection of such medical devices may be problematic, often requiring further surgical intervention, while non-invasive inspection techniques may provide only limited information.

Hence, there is a need to improve provision of articles for use with ionising radiation.

SUMMARY OF THE INVENTION

It is one aim of the present invention, amongst others, to provide which at least partially obviates or mitigates at least some of the disadvantages of the prior art, whether identified herein or elsewhere. For instance, it is an aim of embodiments of the invention to provide a flowable liquid formulation for 3D printing for forming a solidified article having a desired radiopacity and/or regions of differing or graded radiopacity. For instance, it is an aim of embodiments of the invention to provide an article formed by 3D printing comprising a region of a desired radiopacity.

According to a first aspect, there is provided a flowable liquid formulation for 3D printing comprising:
from 0.1 to 25 wt. % radiopaque particles, wherein at least 50% by weight of the particles have a diameter of at most 100 nm; and
monomeric, oligomeric and/or polymeric precursors adapted for polymerization to form a solidified article.

According to a second aspect, there is provided an article formed by 3D printing, the article comprising a first 3D printed region having a first radiopacity and a second 3D printed region having a second radiopacity, wherein the first radiopacity is greater than the second radiopacity.

According to a third aspect, there is provided a method of forming an article by 3D printing comprising:
printing a first 3D printed region having a first radiopacity from a first polymerizable formulation;
printing a second 3D printed region having a second radiopacity from a second polymerizable formulation, wherein the first radiopacity is greater than the second radiopacity;
polymerizing the first polymerizable formulation and the second polymerizable formulation;
wherein the first formulation is according to the first aspect.

According to a fourth aspect, there is provided use of a flowable liquid formulation according to the first aspect to provide a first 3D printed region of a 3D printed article having a radiopacity of at least 400 HU.

DETAILED DESCRIPTION OF THE INVENTION

According to the present invention there is provided a flowable liquid formulation for 3D printing, as set forth in the appended claims. Also provided is an article formed by 3D printing, a method of forming an article by 3D printing and use of a flowable liquid formulation. Other features of the invention will be apparent from the dependent claims, and the description that follows.

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

According to the first aspect, there is provided a flowable liquid formulation for 3D printing comprising:
from 0.1 to 25 wt. % radiopaque particles, wherein at least 50% of the particles have a diameter of at most 100 nm; and
monomeric, oligomeric and/or polymeric precursors adapted for polymerization to form a solidified article.

The flowable liquid formulation maybe known as and/or may be a resin and/or an ink.

Generally, 3D printing, also known as additive manufacturing (AM), refers to processes used to create three-dimensional articles in which layers of material are formed under computer control to create the articles. Stereolithography (SLA) and DLP (Digital Light Processing) are examples of 3D printing processes in which flowable liquid formulations are formed into solidified articles. Photopolymerization is typically used in SLA and/or DLP to form a solid from the liquid formulations. Inkjet SLA and/or DLP printers typically deposit successive layers ultra-thin layers (between 16 and 30 μm) of the photopolymer liquid formulations. Each layer is cured using UV light before deposition of the overlaying layer, producing fully cured articles that may be handled and used immediately, without post-curing. Ultra-small features (<100 nm) may be formed using 3D microfabrication techniques, for example multiphoton photopolymerisation, in which laser beams are used to selectively cure the photopolymer liquid formulations. By using different photopolymer liquid formulations having different respective compositions, articles may be formed by 3D printing to provide regions of the articles having different respective properties. In this way, articles having anisotropic and/or non homogeneous properties, for example structural properties, may be formed by 3D printing.

The flowable liquid formulation of the first aspect is for 3D printing. Generally, flowable liquid formulations for 3D printing may have dynamic or absolute viscosities in a range of from 1 to 100 centipoise or more, as known to the person skilled in the art. Some specialist 3D printers have been designed to 3D print flowable liquid formulations having dynamic or absolute viscosities in a range of 3000 centipoise or more. However, many conventional 3D printers have been designed to 3D print flowable liquid formulations having dynamic or absolute viscosities in a range of from 1 to 100 centipoise. A dynamic viscosity of the flowable liquid formulation may depend, at least in part, on an amount and/or a type of the radiopaque particles in the liquid flowable formulation, such that an increased amount and/or a change of the type of the radiopaque particles may increase the dynamic viscosity. That is, a maximum dynamic viscosity of the flowable liquid formulation suitable for 3D printing may in turn determine, at least in part, a maximum amount and/or a type of the radiopaque particles included therein. Hence, it is desirable that the radiopaque particles are of a type and/or included in an amount that provides a required radiopacity while the flowable liquid formulation has a dynamic viscosity suitable for 3D printing. For example, the flowable liquid formulation preferably has a stable viscosity at a given temperature. For example, the flowable liquid formulation preferably does not develop a significantly non-linear viscosity—shear rate property such as thixotropy. In one example, a dynamic viscosity of the flowable liquid formulation of the first aspect is from 1 to 10,000 centipoise, preferably from 1 to 1000 centipoise, more preferably from 1 to 100 centipoise. The dynamic viscosity may be measured at 20° C., for example using a Brookfield Dial Reading Viscometer model LV, RV or HA in accordance with the manufacturer's instructions.

The flowable liquid formulation comprises from 0.1 to 25 wt. % radiopaque particles, wherein at least 50% by weight of the particles have a diameter of at most 100 nm.

Generally, radiopacity (also known as radiodensity) refers to a relative inability of electromagnetic radiation, particularly X-rays, to pass through a particular material. In contrast, radiolucency (also known as hypodensity) refers to greater transparency or transradiancy of the particular material. Materials that inhibit the passage of electromagnetic radiation are termed radiopaque (also known as radiodense) while materials that allow radiation to pass more freely are termed radiolucent. Radiopaque material tends to appear relatively opaque white in radiography images. While radiopacity is popularly used for qualitative comparison, radiopacity may be quantified according to the Hounsfield scale. On the Hounsfield scale, distilled water has a radiopacity of 0 Hounsfield units (HU), while air is specified as having a radiopacity of −1000 HU. In a medical imaging context, fat has a radiopacity of about −100 HU while blood and muscle have a radiopacity of about 40 HU. In contrast, bone typically has a radiopacity of at least about 400 HU up to about 1200 HU or more. For reference, aluminium has a radiopacity of about 2640 HU. However, determined radiopacities may vary from image-to-image and/or apparatus-to-apparatus, such that differences of about 5-10 HU may not be discernible using conventional apparatuses currently available. Radiopacity for medical imaging may be determined according to ASTM F640 Standard Test Methods for Determining Radiopacity for Medical Use.

The inventors have determined that at such amounts of the radiopaque particles in the formulation of 0.1 to 25 wt. % radiopaque particles, radiopacity of the solidified article may be at least about 400 HU up to about 1200 HU or more and thus comparable with bone, while a dynamic viscosity of the flowable liquid formulation is suitable for 3D printing. Additionally, a uniform dispersion of the radiopaque particles in the flowable liquid formulation may be achieved.

In one example, the radiopaque particles comprise a metal and/or a metal compound, for example a pure or unalloyed metal, an alloy thereof, an inorganic compound such as a ceramic comprising the metal, an organometallic comprising the metal and/or mixtures thereof. The radiopaque particles may comprise a plurality of such metals.

It should be understood that unalloyed metals refer to metals having relatively high purities, for example at least 95 wt. %, at least 97 wt. %, at least 99 wt. %, at least 99.5 wt. %, at least 99.9 wt. %, at least 99.95 wt. %, at least 99.99 wt. %, at least 99.995 wt. % or at least 99.999 wt. % purity.

In one example, the metal is a transition metal, for example a first row, a second row or a third row transition metal. In one example, the metal is Sc, Ti, V, Cr, Mn, Fe, Co, Ni, Cu or Zn. In one example, the metal is Y, Zr, Nb, Mo, Tc, Ru, Rh, Pd, Ag or Cd. In one example, the metal is Hf, Ta, W, Re, Os, Ir, Pt, Au or Hg. In one example, the metal is a lanthanide. In one example, the metal is La, Ce, Pr, Nd, Pm, Sm, Eu, Gd, Tb, Dy, Ho, Er, Tm, Yb or Lu. In one example, the metal is an actinide. In one example, the metal is Ac, Th, Pa, U, Np, Pu, Am, Cm, Bk, Cf or Es.

Generally, the radiopaque particles comprising a metal, for example a pure or unalloyed metal or an alloy thereof, may comprise any metal amenable to fusion by melting. Generally, the radiopaque particles comprising a metal, for example a pure metal or an alloy, may comprise any metal from particles, for example powder particles, may be produced by atomisation. These powder particles may be produced by atomisation, such as gas atomisation or water atomisation, or other processes known in the art.

Inorganic compounds such as ceramics comprising the metal may include, for example, oxides, silicates, sulphides, sulphates, halides, carbonates, phosphates, nitrides, borides, hydroxides of the metal. These inorganic compounds may include a second such metal, for example, mixed oxides such as a mixture of barium titanate and strontium titanate such as $(Ba_x, Sr_{1-x})TiO_3$. The radiopaque particles may comprise TCP (tricalciumphosphate), MCP (monocalciumphosphate), DCP (dicalciumphosphate), tetracalciumphosphate, hydroxylapatite, alpha-TCP, beta-TCP, titanium oxide (titania), aluminium oxide (alumina), zirconium oxide (zirconia), yttrium oxide (yttria), yttria stabilized zirconia, indium oxide, indium tin oxide, boron nitride, silicon carbide, boron carbide, tungsten carbide, beryllium oxide, zeolite, cerium oxide (ceria), tungsten disilicide, sodium silicide, platinium silicide, zirconium nitride, tungsten nitride, vanadium nitride, tantalum nitride, tantalum oxide, niobium nitride, niobium oxide, silicon boride, barium titanate, lead zirconate titanate, zinc oxide, potassium niobate, lithium niobate, sodium tungstate, sodium chloride, sodium nitrate, potassium nitrate, potassium chloride, magnesium chloride, calcium chloride, calcium nitrate, magnesium nitrate, strontium oxide, strontium phosphate, strontium titanate, calcium sulfate, barium sulfate, calcium carbonate, sodium carbonate and/or sodium fluoride or mixtures thereof. The radiopaque particles may comprise silver acetate.

Preferably, the radiopaque particles comprise a transition metal and/or an oxide thereof. More preferably, the radiopaque particles comprise a second row transition metal and/or an oxide thereof, for example zirconium oxide (zirconia), niobium oxide, tantalum oxide and/or silver acetate.

The radiopaque particles may have regular, such as spherical, cuboidal or rod, shapes and/or irregular, such as spheroidal, flake or granular, shapes (also known as morphologies).

The inventors have identified that a size, for example the diameter, of the radiopaque particles (or a largest dimension of an agglomerate) may affect dispersion thereof in the flowable liquid formulation, viscosity of the flowable liquid formulation, jetting during 3D printing and/or radiopacity homogeneity in the solidified article. Non-uniform dispersion in the flowable liquid formulation may result in radiopacity inhomogeneity in the solidified article, such that regions in the solidified material have relatively higher or relatively lower radiopacity than desired. Such radiopacity inhomogeneity in the solidified article is inherently unsuitable for calibration standards, for example, while radiation oncology shields would not provide the required shielding for the intended therapy. Relatively small particles may adversely affect viscosity. Relatively large particles may result in blockages during jetting.

At least 50% by weight of the particles have a diameter of at most 100 nm. For regular shapes, the diameter may refer to the diameter of a sphere or a rod, for example, or to the side of a cuboid. The diameter may also refer to the length of the rod. For irregular shapes, the diameter may refer to a largest dimension, for example, of the particles. Suitably, the particle size distribution is measured by use of light scattering measurement of the particles in an apparatus such as a Malvern Mastersizer 3000, arranged to measure particle sizes from 10 nm to 3500 micrometres, with the particles wet-dispersed in a suitable carrier liquid (along with a suitable dispersant compatible with the particle surface chemistry and the chemical nature of the liquid) in accordance with the equipment manufacturer's instructions and assuming that the particles are of uniform density.

In one example, at least 50% by weight of the radiopaque particles have a diameter at most 100 nm, at most 75 nm, at most 50 nm, at most 25 nm, at most 15 nm, or at most 10 nm. In one example, at least 50% by weight of the radiopaque particles have a diameter of at least 75 nm, at least 50 nm, at least 25 nm, at least 15 nm, or at least 10 nm. In one example, at least 90% by weight of the radiopaque particles have a diameter at most 100 nm, at most 75 nm, at most 50 nm, at most 25 nm, at most 15 nm, or at most 10 nm. In one example, at least 90% by weight of the radiopaque particles have a diameter of at least 75 nm, at least 50 nm, at least 25 nm, at least 15 nm or at least 10 nm. In one example, at least 95% by weight of the radiopaque particles have a diameter at most 100 nm, at most 75 nm, at most 50 nm, at most 25 nm, at most 15 nm or at most 10 nm. In one example, at least 95% by weight of the radiopaque particles have a diameter of at least 75 nm, at least 50 nm, at least 25 nm, at least 15 nm or at least 10 nm. In one example, at least 99% by weight of the radiopaque particles have a diameter at most 100 nm, at most 75 nm, at most 50 nm, at most 25 nm, at most 15 nm or at most 10 nm. In one example, at least 99% by weight of the radiopaque particles have a diameter of at least 75 nm, at least 50 nm, at least 25 nm, at least 15 nm or at least 10 nm.

Particles of these sizes may be termed nanoparticles. Generally, nanoparticles tend to agglomerate, to reduce surface energy. Agglomerates are an assembly of a variable number of the particles and the agglomerates may change in the number of particles and/or shape, for example. Nanopowders are solid powders of nanoparticles, often containing micron-sized nanoparticle agglomerates. These agglomerates can be redispersed (at least to some extent) in the solid state using, for example, ultrasonic processing. Nanoparticle dispersions are suspensions of nanoparticles in a liquid carrier, for example water or organic solvent/organic matrix. Agglomeration may depend, for example, on temperature, pressure, pH-value, and/or viscosity. Agglomeration of the particles may result in non-uniform dispersion of the particles in the flowable liquid formulation and/or radiopacity inhomogeneity of the solidified article. Hence, a suitable particle size may be also a balance between reducing agglomeration while avoiding blockages in use, all while achieving a uniform dispersion and radiopacity homogeneity. Furthermore, a form of the particles (nanopowder or suspension) may affect dispersion in the flowable liquid formulation while the liquid carrier may be incompatible with the polymerization. The inventors have determined that particles of the described sizes, for example provided as nanopowders may provide this appropriate balance.

In one example, the formulation comprises from 0.1 to 25% by weight, preferably from 0.1 to 15 wt. %, more preferably from 1 to 15 wt. %, most preferably from 2 to 15 wt. %, for example from 5 to 10 wt. % radiopaque particles, for example 7 wt. %. The inventors have determined that even at such relatively low amounts of radiopaque particles in the formulation, radiopacity of the solidified article may be at least about 400 HU up to about 1200 HU or more and thus comparable with bone, while a dynamic viscosity of the flowable liquid formulation is suitable for 3D printing. Additionally, a uniform dispersion of the radiopaque particles in the flowable liquid formulation may be achieved.

polyesters. These oligomeric precursors are typically functionalized by acrylate groups. An example shown in Formula I is an epoxy oligomer, functionalized by acrylic acid.

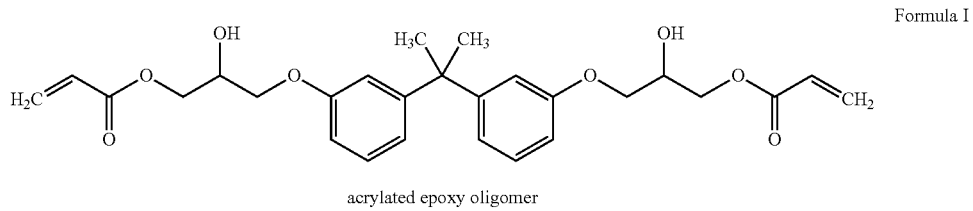 [SMILES: C=CC(=O)OCC(O)COc1cccc(C(C)(C)c2cccc(OCC(O)COC(=O)C=C)c2)c1]

acrylated epoxy oligomer

In one example, the radiopaque particles may comprise or be ZrO₂ particles, Nb₂O₅ particles, Ta₂O₅ particles and/or silver acetate (CH₃CO₂Ag) particles. The inventors have determined that the formulation comprising ZrO₂ particles, Nb₂O₅ particles, Ta₂O₅ particles and/or silver acetate (CH₃CO₂Ag) particles in the amounts described, wherein at least 50% by weight of the ZrO₂ particles, Nb₂O₅ particles, Ta₂O₅ particles and/or silver acetate (CH₃CO₂Ag) particles have a diameter of at most 100 nm, is particularly suitable for 3D printing. Firstly, radiopacity of the solidified article may be at least about 400 HU up to about 1200 HU or more and thus comparable with bone. Secondly, a dynamic viscosity of the flowable liquid formulation is suitable for 3D printing. Thirdly, a uniform dispersion of the radiopaque particles in the flowable liquid formulation may be achieved. Fourthly, ZrO₂ particles, Nb₂O₅ particles, Ta₂O₅ particles and/or silver acetate (CH₃CO₂Ag) particles may exhibit good biocompatibility, for example in vivo biocompatibility, and hence suitable for implantation of the solidified article.

The ZrO₂ particles may comprise monoclinic and/or tetragonal and/or cubic ZrO₂ particles, for example tetragonal ZrO₂ polycrystalline (3Y-TZP) particles. The ZrO₂ particles may comprise fully stabilised ZrO₂ (FSZ) and/or partially-stabilised ZrO₂ (PSZ) particles. Pure ZrO₂ undergoes a phase transformation from monoclinic (stable at room temperature) to tetragonal (at about 1173° C.) and then to cubic (at about 2370° C.). Stabilisation refers to stabilisation of one of these phases of ZrO₂. The ZrO₂ particles may be stabilised and/or partially-stabilised using other metal oxides for example, yttria Y₂O₃, ceria CeO₂, alumina Al₂O₃, calcia CaO and/or hafnia HfO₂. PSZ includes Yttria Stabilized Zirconia (4YSZ), stabilised with 4 mol-% Y₂O₃. FSZ includes Cubic Stabilized Zirconia (CSZ), Yttria Stabilized Zirconia (8YSZ), stabilised with 8 mol-% Y₂O₃ and Yttria Doped Zirconia (8YDZ), doped with 8-9 mol-% Y₂O₃.

The monomeric, oligomeric and/or polymeric precursors are adapted for polymerization, also known as curing, to form the solidified article. For example, the polymerization may be initiated by electromagnetic radiation, heat and/or chemical activation.

Generally, polymerization initiated by UV radiation is known as photopolymerization and the monomeric, oligomeric and/or polymeric precursors adapted for photopolymerization may be known collectively as photopolymers. Polymerization by visible radiation may be enabled by dye-based photoinitiators, for example. Initiation of photopolymerization may be by free radical and/or ionic mechanisms.

Typically, some properties of the solidified articles, such as flexibility, adhesion, and chemical resistance, are due at least in part to the oligomeric precursors. The oligomeric precursors are typically epoxides, urethanes, polyethers, or polyesters. These oligomeric precursors are typically functionalized by acrylate groups. An example shown in Formula I is an epoxy oligomer, functionalized by acrylic acid.

The oligomeric precursors may comprise a urethane (meth)acrylate oligomer, a polyester (meth)acrylate, an epoxy (meth)acrylate oligomer, or a combination thereof. The oligomeric precursors may comprise one or more ethylenically unsaturated moieties.

The monomeric precursors may control, at least in part, curing speed, crosslink density, surface properties, and/or viscosity of the flowable liquid formulation. Examples of monomeric precursors include styrenes, N-vinylpyrrolidone and acrylates (also known as acrylic monomers). Typically, styrenes are low cost and provide fast curing. Typically, N-vinylpyrrolidone has low toxicity. Typically, acrylates are highly reactive, providing fast curing, and may be highly versatile with functionality ranging from monofunctional to tetrafunctional.

The monomeric precursor may comprise a monofunctional (meth)acrylate, a difunctional (meth)acrylate, a trifunctional (meth)acrylate, a tetrafunctional (meth)acrylate, a pentafunctional (meth)acrylate, or a combination thereof. Acrylic monomeric precursors are preferred.

Polymerizable monomeric, oligomeric and/or polymeric precursors including an acrylate group include, but are not limited to, mono-, di- or poly-acrylates and methacrylates and esters thereof such as methyl acrylate, methyl methacrylate, methacrylic acid, ethyl acrylate, ethyl methacrylate, isopropyl methacrylate, tert-butyl (meth)acrylate, cyclohexyl (meth)acrylate, 4-tert-butylcyclohexyl (meth)acrylate, tetrahydrofurfuryl (meth)acrylate, n-hexyl acrylate, 2-phenoxyethyl (meth)acrylate, stearyl acrylate, allyl acrylate, isobornyl (meth)acrylate, stearyl (meth)acrylate, phenoxy benzyl (meth)acrylate, o-phenylphenol ethyl (meth)acrylate, tris (2-hydroxy ethyl) isocyanurate diacrylate, the reaction product of octadecyl isocyanate and caprolactone 2-(methacryloyloxy)ethyl ester, the reaction product of octadecyl isocyanate and 2-hydroxyethyl acrylate; the reaction product of octadecyl isocyanate and hydroxypropyl (meth)acrylate; the reaction product of octadecyl isocyanate and 2-hydroxypropyl 2-(methacryloyloxy)-ethyl phthalate; the reaction product of octadecyl isocyanate and 2-hydroxy-3-phenoxypropyl acrylate; the reaction product of octadecyl isocyanate and glycerol dimethacrylate; the reaction product of octadecyl isocyanate and pentaerythritol triacrylate; the reaction product of cyclohexyl isocyanate and 2-hydroxyethyl (meth)acrylate; the reaction product of benzyl isocyanate and 2-hydroxyethyl (meth)acrylate; 1, 14-tetradecanedimethacrylate, dimethylol tricyclodecane diacrylate, glycerol diacrylate, glycerol triacrylate, ethylene glycol diacrylate, diethyleneglycol diacrylate, triethyleneglycol dimethacrylate, tetraethylene glycol di(meth)acrylate, 1, 3-propanediol diacrylate, 1, 3-propanediol dimethacrylate, trimethylolpropane tri(meth)acrylate, 1, 2,4-butanetriol trimethacrylate, 1, 4-cyclohexanediol] diacrylate, 1, 4-cyclohexanediol dimethacrylate, 6-hexanediol di(meth)acrylate, pentaerythritol triacrylate, pentaerythritol tetraacrylate, pentaerythritol tetramethacrylate, sorbitol hexacrylate, 2,2-bis[4-{2-hydroxy-3-acryloyloxypropoxy)phenyl]propane; 2,2-bis[4-(2-hydroxy-3-methacryloyloxypropoxy)phenyl] propane (Bis-GMA); the reaction product of Bis-GMA and octadecyl isocyanate; the reaction product of Bis-GMA and cyclohexyl isocyanate; 2,2-bis[4-(acryloyloxy-ethoxy)phenyl]propane; 2,2-bis[4-(methacryloyloxy-ethoxy)phenyl] propane (or ethoxylated bisphenol A-dimethacrylate) (EB-PADMA); urethane di{meth)acrylate (UDMA), diurethane dimethacrylate (DUDMA), 4, 3-dioxo-3,14 dioxa-5,12-diazahexadecane-1, 16-diol diacrylate; 4, 13-dioxo-3, 14 dioxa-5,12-diazahexadecane-1, 16-diol dimethacrylate; 4,19-dioxo-3,20 dioxa-5,18-diazahexadecane-1, 22-diol diacrylate; 4,19-dioxo-3,20 dioxa-5, 18-diazahexadecane-1, 22-diol dimethacrylate; the reaction product of trimethyl 1, 6-diisocyanatohexane and bisphenol A propoxylate and 2-hydroxyethyl methacrylate (TBDMA); the reaction product of 1, 6 diisocyanatohexane and 2-hydroxyethyl methacrylate modified with water (HDiDMA); the reaction product of 1, 6 diisocyanatohexane and 2-hydroxyethyl acrylate modified with water (HDIDA); the reaction product of 1, 6-diisocyanatohexane, 1, 2-decanediol, 1, 10-decanediol and 2-hydroxyethyl (meth)acrylate; the reaction product of 1, 6-diisocyanatohexane, 3-hydroxy 2,2-dimethylpropyl 3-hydroxy-2,2-dimethyl propionate, 1, 10-decanediol and 2-hydroxyethyl (meth)acrylate; the reaction product of 1, 6-diisocyanatohexane, 1, 0-decanediol and 2-hydroxyethyl (meth)acrylate; the reaction product of 1, 6-diisocyanatohexane, 1, 2-decanediol, 1, 10-decanedioi, 3-hydroxy 2,2-dimethylpropyl 3-hydroxy-2,2-dimethyl propionate and 2-hydroxyethyl (meth)acrylate; the reaction product of 1, 6-diisocyanatohexane, trimethyl 1, 6-diisocyanatohexane, 1, 10-decanediol and 2-hydroxyethyl (meth)acrylate; the reaction product of 1, 6-diisocyanatohexane, trimethyl 1, 6-diisocyanatohexane, 3-hydroxy 2,2-dimethylpropyl 3-hydroxy-2,2-dimethyl propionate, 1, 10-decanedioi and 2-hydroxyethyl (meth)acrylate; the reaction product of 1, 6-diisocyanatohexane, 2,5-dimethyl-2,5-hexanediol and 2-hydroxyethyl (meth)acrylate; the reaction product of 1, 6-diisocyanatohexane, 4,4'-isopropylidenedicyclohexanol and 2-hydroxyethyl (meth)acrylate; the reaction product of 1, 6-diisocyanatohexane, 1, 2-decanediol, 1, 10-decanediol, 3-hydroxy 2,2-dimethylpropyl 3-hydroxy-2,2-dimethyl propionate and 2-hydroxyethyl (meth)acrylate; the reaction products of 2-isocyanatoethyl methacrylate and diols; polyurethane dimethacrylate (PUDMA); alkoxylated pentacrythritol tetraacrylate; polycarbonate dimethacrylate (PCDMA); the bis-acrylates and bis-methacrylates of polyethylene glycols; (meth)acrylate modified silicones; light curable epoxides; epoxy methacrylate (or acrylate), methacrylate (or acrylate) compounds or their combinations; various epoxides in combination with various diols [such as 1, 3-bis(3-glycidyloxypropyl)tetramethyldisoxane, bisphenol A proxylate diglycidyl ether, bis(3,4-epoxy-6-methylcyclohexylmethyl)adipate, 1, 10 decanediol, 1, 6-hexanediol, branched diol, aromatic diol, bisphenol A, proxylated bisphenol A, etc.; and copolymerizable mixtures of acrylated monomers and acrylated oligomers. Monomeric and/or oligomeric and/or polymeric precursors including an acrylate group are preferred, for example acrylic monomers, isobornyl (meth) acrylate, phenol, 4,4'-(1-methylethylidene)bis-, polymer with (chloromethyl)oxirane, 2-propenoate.

In one example, the monomeric, oligomeric and/or polymeric precursors are photopolymerizable precursors adapted for polymerization to form the solidified article by irradiation, for example by ultraviolet (UV) curing.

In one example, the formulation comprises from 40 to 80 wt. % monomeric, oligomeric and/or polymeric precursors, for example monomeric and/or oligomeric and/or polymeric precursors including an acrylate group.

In one example, the formulation comprises from 20 to 60 wt. % monomeric precursors, for example monomeric precursors including an acrylate group for example acrylic monomers, isobornyl (meth)acrylate.

In one example, the formulation comprises from 5 to 25 wt. % oligomeric precursors, for example oligomeric precursors including an acrylate group such as phenol, 4,4'-(1-methylethylidene)bis-, polymer with (chloromethyl)oxirane, 2-propenoate (also known as Bisphenol A-epichlorohydrin acrylate, Bisphenol A-epichlorohydrin copolymer acrylate, Bisphenol A-epichlorohydrin polymer acrylate, AED 30, AED 60, Araldite AER 2603 acrylate, Araldite GT 7004 acrylate and epoxy resin, amongst others).

In one example, the formulation comprises at least one of a photoinitiator, a retarder solvent, a filler, an additive and a colouring agent.

Generally, photoinitiators generate radicals by UVNis light to initiate polymerization, for example by crosslinking of unsaturated hydrocarbons. Examples of photoinitiators include benzoylphosphine oxides for example diphenyl(2, 4,6-trimethylbenzoyl)phosphine oxide (CAS 75980-60-8), bis(2,4,6-trimethyl benzoyl)phenyl phosphine oxide (IRGACURE 819), 2,4,6-trimethylbenzoyl diphenyl phosphine (TPO), 2-hydroxy-2-methyl-1-phenyl-1-propane (DAROCUR 1173), benzophenone (BP). Non-curable photoinitiators comprise an alpha-cleavage type (unimolecular decomposition process) photoinitiator or a hydrogen abstraction photosensitizer-tertiary amine synergist, operable to absorb light between about 250 nm and about 400 nm or between about 300 nm and about 385 nm, to yield free radical(s). Examples of alpha cleavage photoinitiators are Irgacure 184 (CAS 947-19-3), Irgacure 369 (CAS 119313-12-1), and Irgacure 819 (CAS 162881-26-7). An example of a photosensitizer-amine combination is Darocur BP (CAS 119-61-9) with diethylaminoethylmethacrylate.

In one example, the formulation comprises a photoinitiator in an amount of at least 0.001 wt. %, at least 0.01 wt. %, at least 0.1 wt. %, at least 1 wt. % or at least 2 wt. % by weight of the formulation. In one example, the formulation comprises a photoinitiator in an amount of at most 0.001 wt. %, at most 0.01 wt. %, at most 0.1 wt. %, at most 1 wt. %, at most 2 wt. % or at most 5 wt. % by weight of the formulation.

Generally, retarder solvents are slow drying solvents that may be optionally included in flowable liquid formulations for 3D printing to improve surface quality, for example. Examples of retarder solvents include Propylene Glycol Monomethyl Ether Acetate (PMA), Methyl n-Amyl Ketone (MAK) and xylene.

In one example, the formulation comprises a retarder solvent in an amount of at least 0.001 wt. %, at least 0.01 wt. %, at least 0.1 wt. %, at least 1 wt. % or at least 2 wt. % by weight of the formulation. In one example, the formulation comprises a retarder solvent in an amount of at most 0.001 wt. %, at most 0.01 wt. %, at most 0.1 wt. %, at most 1 wt. %, at most 2 wt. % or at most 5 wt. % by weight of the formulation.

Generally, colouring agents may be included to provide a colour to the flowable liquid formulation and/or the solidified article. The colouring agents may include organic and/or inorganic pigments, for example. Examples of organic pigments include Cromophtal Red-BRN 2-napthalenecarboxamide, azo pigments, polyazo pigments, azomethine pigments, isoindoline pigments, anthraquinone pigments, phthalocyanine pigments and benzimidazolone pigments. Examples of inorganic pigments include black iron oxide, yellow iron oxide, ultramarine blue, brown iron oxide, titanium dioxide, zinc flower, zinc oxide, iron oxide, aluminium oxide, silicon dioxide, talc, barium sulfate, calcium sulfate, red oxide, cobalt chrome green, Armenian blue, carbon black, mica, cobalt violet, molybdenum red, titanium cobalt green, and molybdate orange.

In one example, the formulation comprises a colouring agent in an amount of at least 0.001 wt. %, at least 0.01 wt. %, at least 0.1 wt. %, at least 1 wt. % or at least 2 wt. % by weight of the formulation. In one example, the formulation comprises a colouring agent in an amount of at most 0.001 wt. %, at most 0.01 wt. %, at most 0.1 wt. %, at most 1 wt. %, at most 2 wt. % or at most 5 wt. % by weight of the formulation.

In one example, the formulation comprises an acid catalyst. Examples of acid catalysts include aliphatic carboxylic acids, such as acetic acid, chloroacetic acid, trichloroacetic acid, trifluoroacetic acid, oxalic acid, maleic acid, malonic acid, lactic acid and citric acid; aromatic carboxylic acids, such as benzoic acid, phthalic acid, terephthalic acid and trimellitic acid; aliphatic and aromatic sulfonic acids, such as methanesulfonic acid, dodecylsulfonic acid, benzenesulfonic acid, dodecylbenzenesulfonic acid, naphthalenesulfonic acid, p-toluenesulfonic acid, dinonylnaphthalenesulfonic acid (DNNSA), dinonylnaphthalenedisulfonic acid (DNNDSA) and phenolsulfonic acid; and phosphoric acid and mixtures thereof.

In one example, the formulation comprises an acid catalyst in an amount of at least 0.001 wt. %, at least 0.01 wt. %, at least 0.1 wt. %, at least 1 wt. % or at least 2 wt. % by weight of the formulation. In one example, the formulation comprises an acid catalyst in an amount of at most 0.001 wt. %, at most 0.01 wt. %, at most 0.1 wt. %, at most 1 wt. %, at most 2 wt. % or at most 5 wt. % by weight of the formulation.

A preferred formulation according to the first aspect comprises:
- from 1 to 15 wt. % radiopaque particles, wherein at least 50% by weight of the particles have a diameter of at most 100 nm, wherein at least 50%, preferably at least 75%, more preferably at least 90% by weight of the particles comprises a second-row transition metal oxide, for example zirconium oxide, niobium oxide, tantalum oxide and/or silver acetate;
- monomeric, oligomeric and/or polymeric precursors adapted for photopolymerization to form a solidified article, wherein the monomeric, oligomeric and/or polymeric precursors comprise acrylate groups; and
- wherein the formulation comprises at least one of a photoinitiator, a retarder solvent, a filler, an additive and a colouring agent.

This preferred formulation is particularly suitable for the other aspects, as set out below.

According to the second aspect, there is provided an article formed by 3D printing, the article comprising a first 3D printed region having a first radiopacity and a second 3D printed region having a second radiopacity, wherein the first radiopacity is greater than the second radiopacity.

In this way, the article may be formed by 3D printing having two 3D printed regions, having different radiopacities. By forming the article by 3D printing, complex structures having complex internal features, for example provided by the first 3D printed region, may be provided.

In one example, the article comprises a plurality of 3D printed regions having different radiopacities. For example, the article may comprise a plurality of first 3D printed regions having respective first radiopacities, wherein the respective first radiopacities are greater than the second radiopacity.

In one example, the first 3D printed region is obtained by polymerisation of the formulation according to the first aspect.

In one example, the article is a calibration standard for a medical radiography apparatus. In this way, calibration standards may be formed by 3D printing more reliably, reproducibly or repeatably and/or more complex calibration standards may be formed by 3D printing. In this way, calibration standards may be formed by 3D printing for apparatus calibration, for example custom calibration standards. Additionally, and/or alternatively, medically-relevant calibration standards may be formed by 3D printing, for example, fracture samples for calibration and/or teaching purposes. Such medically-relevant calibration standards are typically provided from biological sources, thus giving rise to variations between nominally equivalent medically-relevant calibration standards. In contrast, by forming calibration standards by 3D printing, variation between nominally equivalent medically-relevant calibration standards may be reduced while 3D printing may allow forming of relatively complex samples.

In one example, the article is a medical device. For example, the medical device may be a catheter tip, a marking band, an orientation guide, a stent marker, a prosthetic heart valve, a pacemaker, a filter, a coil or an occlusion device. For example, the medical device may be a position guide for an orthopaedic application, such as a cutting guide or an alignment jig. For example, the medical device may be a positioning jig and/or shield for an oncological application, for example conformal radiotherapy, intensity-modulated radiotherapy, stereotactic radiotherapy, image-guided radiotherapy, hyper fractionated or hypo fractionated radiotherapy.

In one example, the first radiopacity is at least 400 Hounsfield Units (HU) and/or the first radiopacity is greater than the second radiopacity by at least 5 HU. That is, the first radiopacity may be similar to that of bone and hence may appear similarly to bone during medical imaging. The difference between the first radiopacity and the second radiopacity of at least 5 HU may enable the first 3D printed region to be visibly distinguished in a medical image from the second 3D printed region, using current medical radiography apparatus.

In one example, the first radiopacity is at least 400 HU, preferably at least 500 HU, more preferably at least 600 HU. In one example, the first radiopacity is at most 1200 HU, preferably at most 1000 HU, more preferably at most 800 HU.

In one example, the second radiopacity is at least 200 HU, preferably at least 250 HU, more preferably at least 300 HU. In one example, the second radiopacity is at most 1200 HU, preferably at most 1000 HU, more preferably at most 800 HU.

In one example, the first radiopacity is greater than the second radiopacity by at least 1 HU, at least 2 HU, at least 3 HU, at least 4 HU, at least 5 HU, at least 6 HU, at least 7 HU, at least 8 HU, at least 9 HU or at least 10 HU, according to a performance of the medical radiography apparatus, for example. In one example, the first radiopacity is greater than the second radiopacity by at most 1 HU, at most 2 HU, at most 3 HU, at most 4 HU, at most 5 HU, at most 6 HU, at most 7 HU, at most 8 HU, at most 9 HU or at most 10 HU, according to a performance of the medical radiography apparatus, for example. In one example, the first radiopacity is greater than the second radiopacity by at least 10 HU, at least 20 HU, at least 30 HU, at least 40 HU, at least 50 HU, at least 60 HU, at least 70 HU, at least 80 HU, at least 90 HU or at least 100 HU, according to a performance of the medical radiography apparatus, for example. In one example, the first radiopacity is greater than the second radiopacity by at most 10 HU, at most 20 HU, at most 30 HU, at most 40 HU, at most 50 HU, at most 60 HU, at most 70 HU, at most 80 HU, at most 90 HU or at most 100 HU, according to a performance of the medical radiography apparatus, for example.

In one example, the first 3D printed region having the first radiopacity provides a marker, for example a positioning marker and/or an identifying marker. In this way, the marker may be integrated into the article, for example embedded in the article such as surrounded and/or completely surrounded by the second 3D printed region having the second radiopacity. That is, the marker may be an internal marker. In this way, the marker may be discernible or visible upon medical imaging, for example radiography, allowing identification of the marker and/or confirmation of an orientation of the article according to an orientation of the marker, for example. For example, the marker may be a serial number or a graphic symbol.

In one example, the first 3D printed region of the 3D printed article provides at least in part, comprises and/or is an identifier of the 3D printed article.

According to the third aspect, there is provided a method of forming an article by 3D printing comprising:
    printing a first 3D printed region having a first radiopacity from a first polymerizable formulation;
    printing a second 3D printed region having a second radiopacity from a second polymerizable formulation, wherein the first radiopacity is greater than the second radiopacity;
    polymerizing the first polymerizable formulation and the second polymerizable formulation;
    wherein the first formulation is according to the first aspect.

In one example, the method comprises dispersing the radiopaque particles in the first formulation by shear mixing.

In one example, polymerizing the first polymerizable formulation and the second polymerizable formulation comprises photopolymerizing the first polymerizable formulation and/or the second polymerizable formulation.

In one example, the method comprises mixing the first formulation and the second formulation to provide a mixed formulation and printing another first 3D printed region having another first radiopacity from the mixed formulation.

In one example, the method comprises printing a first voxel of the first formulation and printing a second voxel of the second formulation adjacent to the first voxel.

In one example, the first radiopacity is at most 400 Hounsfield Units (HU) and/or the first radiopacity is greater than the second radiopacity by at least 5 HU.

The article may be according to the second aspect.

According to the fourth aspect, there is provided use of a flowable liquid formulation according to the first aspect to provide a first 3D printed region of a 3D printed article having a radiopacity of at least 400 HU.

In one example, the 3D printed article is a calibration standard for a medical radiography apparatus.

In one example, the 3D printed article is a medical device.

In one example, the first 3D printed region of the 3D printed article provides at least in part, comprises and/or is an identifier of the 3D printed article.

The article may be according to the second aspect.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which.

DETAILED DESCRIPTION OF THE DRAWINGS

Generally, like reference signs denote like features, description of which is not repeated for brevity.

Figure 1:
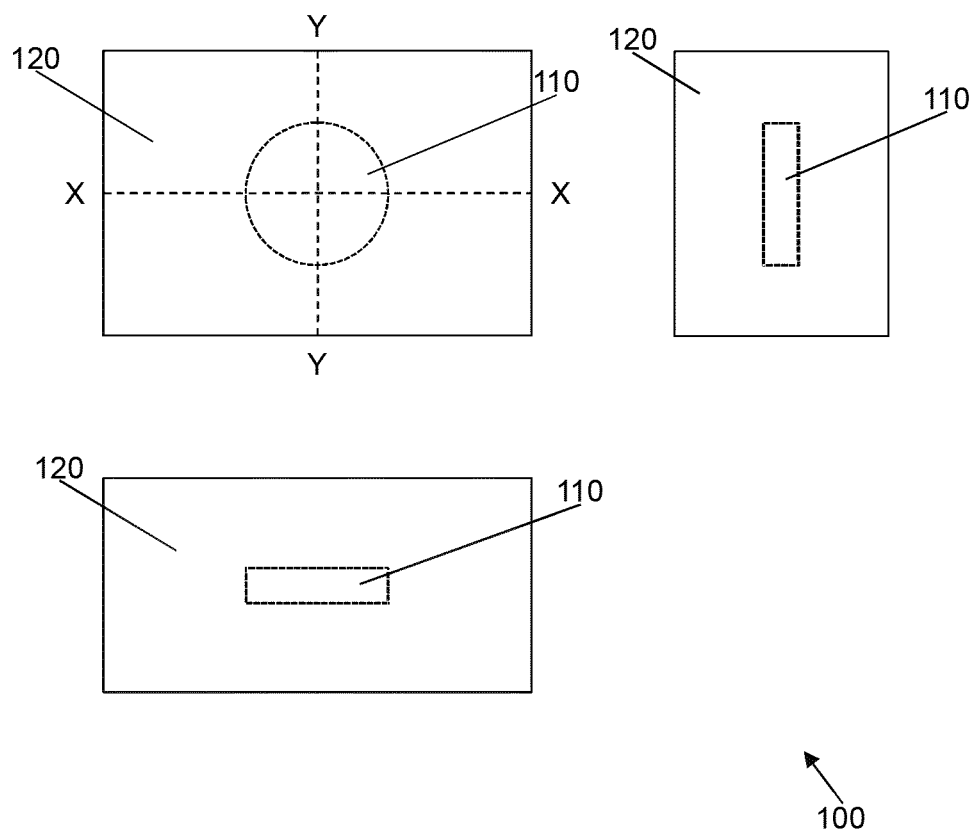
FIG. 1 schematically depicts an article according to an exemplary embodiment.

FIG. 1 schematically depicts an article 100 according to an exemplary embodiment. Particularly, FIG. 1 schematically depicts plan, front and side elevation views of the article 100.

The article 100 is formed by 3D printing. The article 100 comprises a first 3D printed region 110 having a first radiopacity and a second 3D printed region 120 having a second radiopacity, wherein the first radiopacity is greater than the second radiopacity.

In this way, the article 100 may be formed by 3D printing having two 3D printed regions 110, 120, having different radiopacities. By forming the article 100 by 3D printing, complex structures having complex internal features, for example provided by the first 3D printed region 110, may be provided.

In more detail, the article 100 is cuboidal, having dimensions 60×40×30 mm (length×width×height). The first 3D printed region 110 having the first radiopacity is a cylindrical disc, having dimension of 20×5 mm (diameter×thickness) and is arranged centrally in the article 100, having circular faces parallel to the relatively larger 60×40 rectangular faces of the article 100. The second 3D printed region 120 having the second radiopacity provides the remainder of the article 100. That is, the first 3D printed region 110 is internal to the article 100, completely surrounded by and/or embedded in the second 3D printed region 120.

Figure 2A:
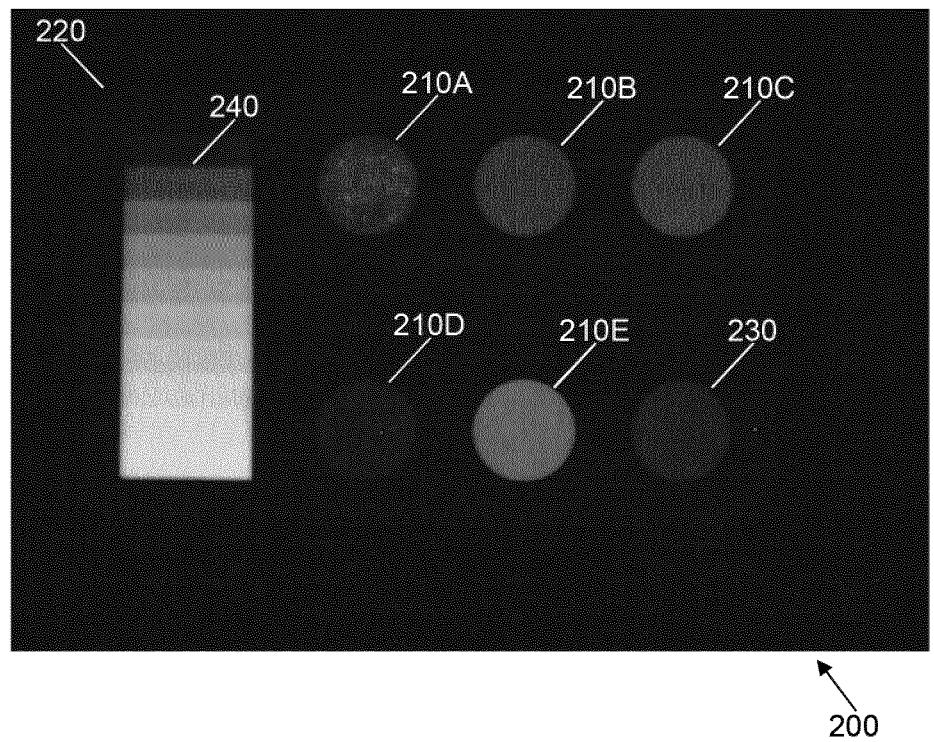
FIGS. 2A-2B depict an article according to an exemplary embodiment.
Figure 2B:
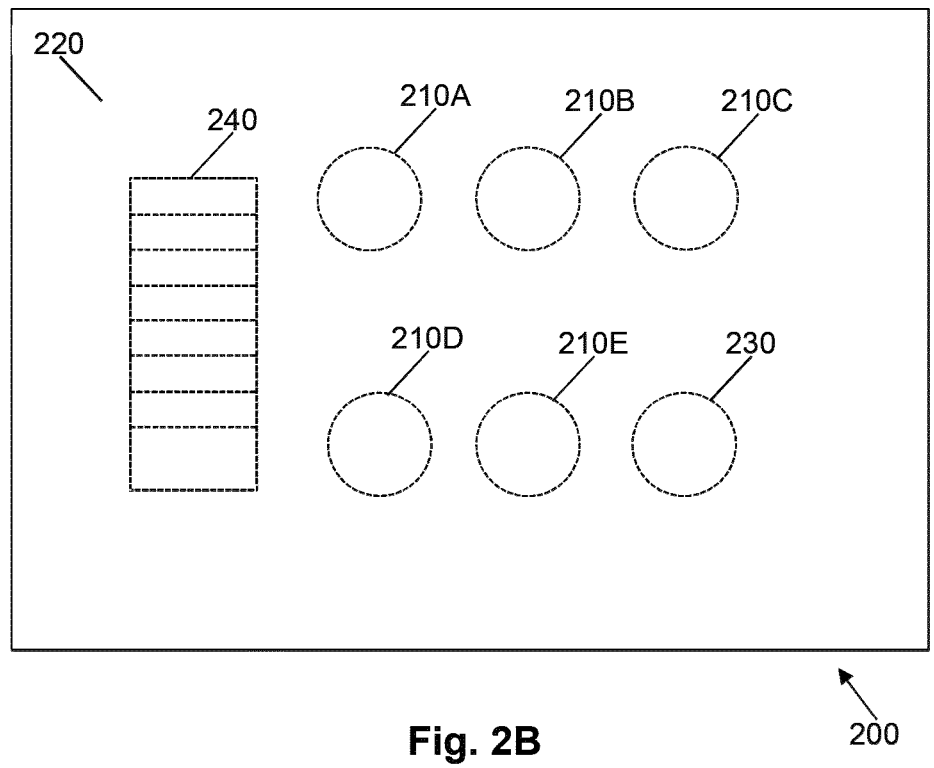

FIGS. 2A and 2B depict an article 200 according to an exemplary embodiment. Particularly, FIG. 2A depicts a radiograph of the article 200 and FIG. 2B schematically depicts a corresponding plan view of the article 200.

The article 200 is formed by 3D printing. The article 200 comprises a first 3D printed region 210 having a first radiopacity and a second 3D printed region 220 having a second radiopacity, wherein the first radiopacity is greater than the second radiopacity.

In more detail, the article 200 comprises five first 3D printed regions 210A-210E having different first radiopacities, increasing in the order from the first 3D printed region 210A to the first 3D printed region 210E. Similar to the first 3D printed region 110 of the article 100 described above, the five first 3D printed regions 210A-210E are cylindrical discs, internal to the article 200, completely surrounded by and/or embedded in the second 3D printed region 220. The five first 3D printed regions 210A-210E are arranged spaced apart in a regular array in the article 200.

The article 200 further comprises a porcine bone sample 230, having similar dimensions to the five first 3D printed regions 210A-210E and similarly arranged. The porcine bone sample 230 has a radiopacity of about 400 HU. The article 200 further comprises a conventional calibration standard 240 in the form of a step wedge according to ASTM F640 Standard Test Methods for Determining Radiopacity for Medical Use.

The second 3D printed region 220 having the second radiopacity provides the remainder of the article 200.

The second 3D printed region 220 is formed by 3D printing using a Connex500 3D printer available from Stratasys Ltd. (USA) and a 3D printer ink OBJET VEROWHITEPLUS RGD835, available from Objet, Inc. (USA), having a composition detailed in Table 1 (i.e. a second polymerizable formulation).

TABLE 1

Composition of OBJET VEROWHITEPLUS RGD835 ink

| CAS | Component | | Wt. % |
|---|---|---|---|
| — | Acrylic monomer | monomeric precursor | <30 |
| 5888-33-5 | Isobornyl acrylate | monomeric precursor | <25 |
| — | Phenol, 4,4'-(1-methylethylidene)bis-, polymer with (chloromethyl)oxirane, 2-propenoate | oligomeric precursor | <15 |
| — | Diphenyl-2,4,6-trimethylbenzoyl phosphine oxide | photoinitiator | <2 |
| 13463-67-7 | Titanium dioxide | colouring agent | <0.8 |
| 52408-84-1 | Acrylic acid ester | monomeric precursor | <0.3 |
| 108-65-6 | Propylene glycol monomethyl ether acetate | retarder solvent | 0.1-0.125 |
| 7664-38-2 | Phosphoric acid | acid catalyst | 0.002-0.015 |

The five first 3D printed regions 210A-210E are formed by 3D printing using the 3D printer ink OBJET VEROWHITEPLUS RGD835 including from 0.1 to 25 wt. % radiopaque particles comprising $ZrO_2$ particles, wherein at least 50% of the $ZrO_2$ particles have a diameter of at most 100 nm (i.e. a flowable liquid formulation for 3D printing, a second polymerizable formulation). The $ZrO_2$ particles are available from Sigma Aldrich as 544760 Aldrich Zirconium (IV) oxide nanopowder <100 nm particle size (as determined by TEM).

The five first 3D printed regions 210A-210E are formed by 3D printing the flowable liquid formulation comprising different amounts of the $ZrO_2$ particles, thereby providing different first radiopacities.

Particularly, radiopacities of the various regions increase in an order the second 3D printed region 220, the first 3D printed region 210D, the porcine bone sample 230, the first 3D printed region 210A, the first 3D printed region 210B, the first 3D printed region 210C and the first 3D printed region 210E. That is, the first 3D printed region 210A, the first 3D printed region 210B, the first 3D printed region 210C and the first 3D printed region 210E have radiopacities greater than that of the porcine bone sample 230 (about 400 HU) while the first 3D printed region 210D has a radiopacity less than that of the porcine bone sample 230.

In this way, the article 200 may provide a calibration standard for a medical radiography apparatus by comprising the five first 3D printed regions 210A-210E formed by 3D printing.

Figure 3:
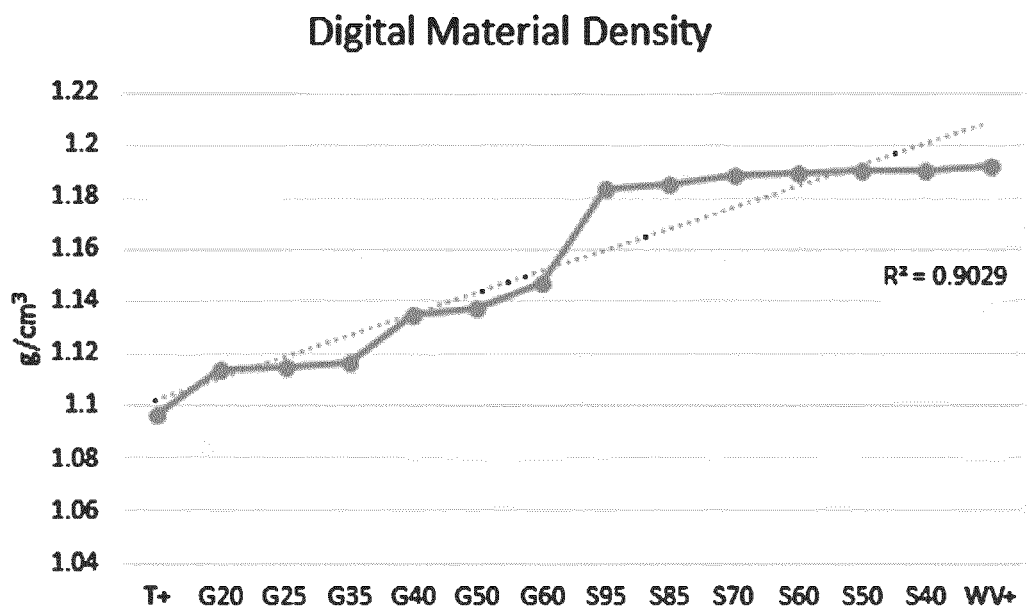
FIG. 3 schematically depicts a graph of density as a function of composition of second 3D printed regions according to exemplary embodiments.

FIG. 3 schematically depicts a graph of density as a function of composition of second 3D printed regions. Particularly, FIG. 3 shows densities of 14 different second 3D printed regions, formed by 3D printing commercial resins T+, G20, G25, G35, G40, G50, G60 S95, S85, S70, S60, S50, S40 and WV+, available from Objet, Inc. (USA). These commercial resins do not include radiopaque particles. Densities are in a range of about 1.1 to about 1.2 $g/cm^3$, with an average density of about 1.15 $g/cm^3$. By including $ZrO_2$ particles, having a density of about 5.68 $g/cm^3$, in these resins, an average density of a first 3D printed region printed therefrom is increased to about 1.2 $g/cm^3$ for a 1 wt. % loading of the particles, about 1.38 $g/cm^3$ for a 5 wt. % loading of the particles and about 1.83 $g/cm^3$ for a 15 wt. % loading of the particles.

Figure 4A:
FIGS. 4A-4D schematically depict an article according to an exemplary embodiment.
Figure 4B:
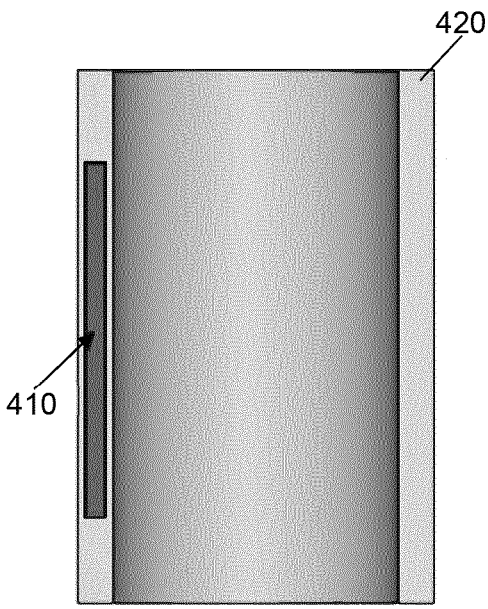
Figure 4C:
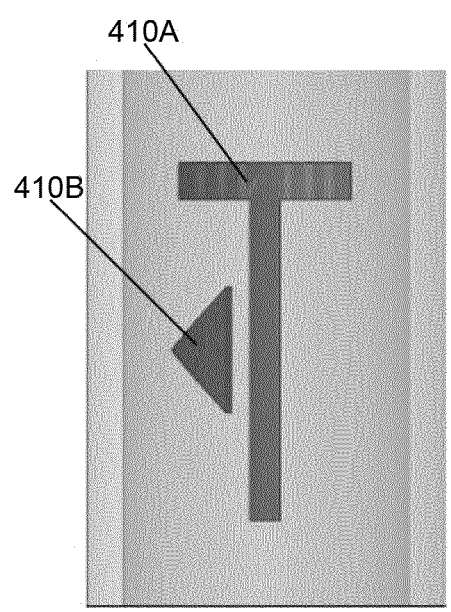
Figure 4D:
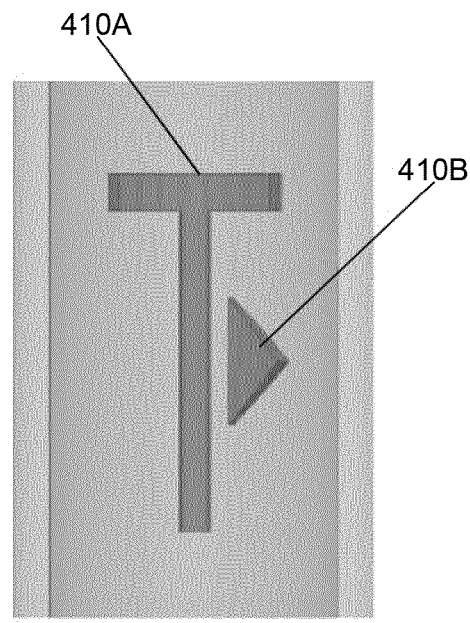

FIGS. 4A-4D schematically depict an article 400 according to an exemplary embodiment. Particularly, FIG. 4A schematically depicts a projection view of the article 400, FIG. 4B schematically depicts a cross sectional view of the article 400, FIG. 4C schematically depicts a front elevation view of the article 400 and FIG. 4D schematically depicts a rear elevation view of the article 400. The article 400 is formed by 3D printing. The article 400 comprises a first 3D printed region 410 having a first radiopacity and a second 3D printed region 420 having a second radiopacity, wherein the first radiopacity is greater than the second radiopacity.

In more detail, the article 400 a circular tube. The article 400 comprises two first 3D printed regions 410A-410B having the same first radiopacities. Similar to the first 3D printed region 110 of the article 100 described above, the two first 3D printed regions 410A-410B are internal to the article 400, completely surrounded by and/or embedded in the second 3D printed region 420. The two first 3D printed regions 410A-410B provide markers, particularly integrated, radiopaque positioning markers. The first 3D printed region 410A is in the form of a T. The first 3D printed region 410B is in the form of an arrow or triangle.

FIGS. 4C-4D schematically depict how the two first 3D printed regions 410A-410B printed internally in the article 400 indicate orientation of the article 400 during medical imaging, for example under X-ray imaging (such as fluoroscopy). When the arrow 410B points to the left, the article 400 is oriented correctly. In contrast, when the arrow 410B points to the right, the article 400 is oriented upside down. This type of marker is of particular benefit in delivery systems for prosthetic heart valves, pacemakers, filters, coils or occlusion devices, for example.

Figure 5A:
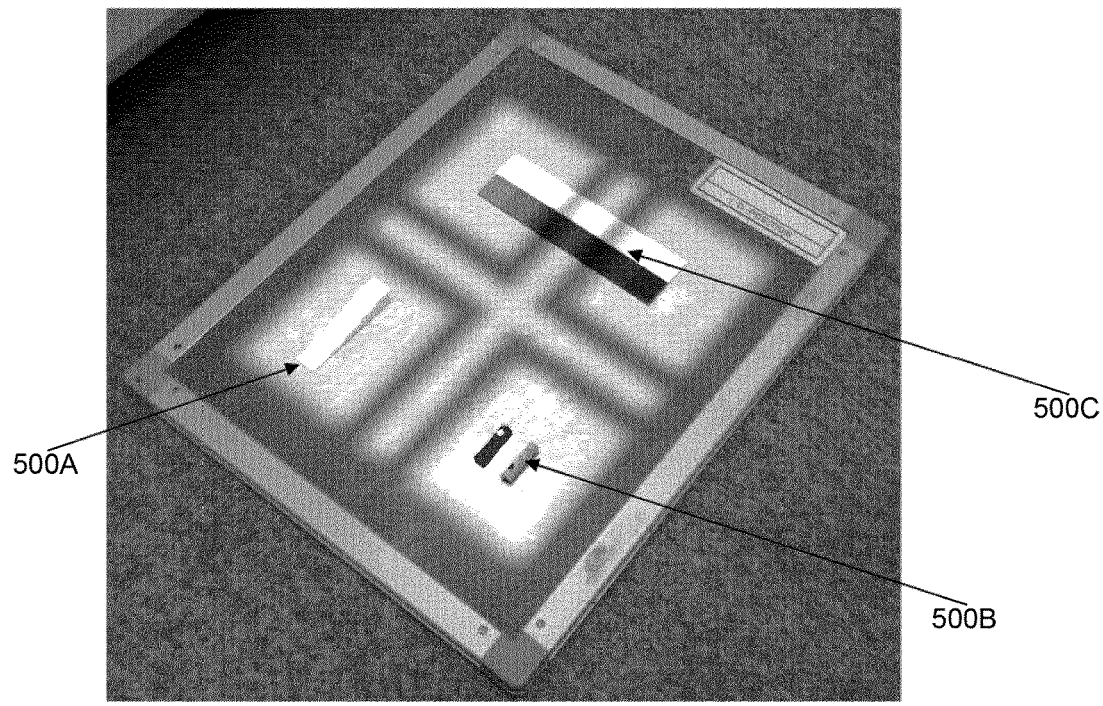
FIGS. 5A-5B depict articles according to exemplary embodiments.
Figure 5B:
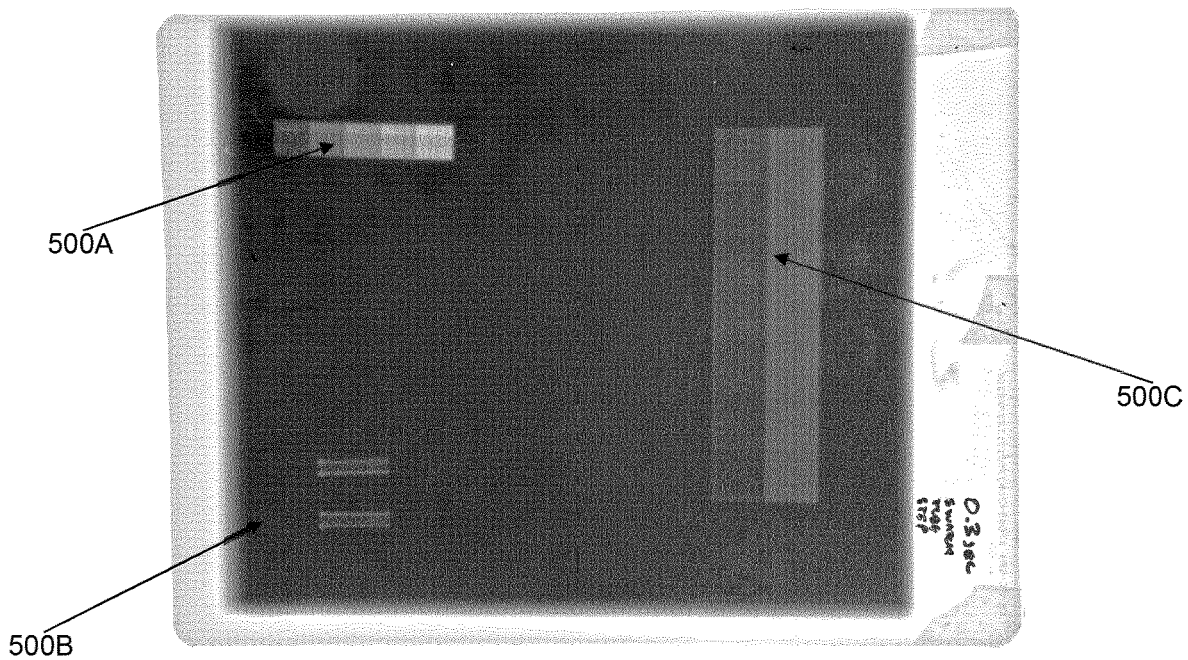

FIGS. 5A-5B depict articles according to exemplary embodiments. Particularly, FIG. 5A shows a photograph of three articles 500A-500C according to exemplary embodiments. FIG. 5B shows a radiograph of the three articles 500A-500C, imaged using an Americomp F280 X-ray system, 50 kV tube voltage, 50 mA current and 80 cm focal length on plain film with an exposure time of 0.1-0.3 seconds. The radiograph image was captured on MG-SR Plus X-ray film (Konica Minolta), digitally photographed and tone adjusted in Adobe Photoshop. It should be understood that tone adjustment is made to all of the image including any reference, for example an aluminium stepped part and/or a porcine sample, such that radiopacities, relative to the reference are not be affected.

Figure 6A:
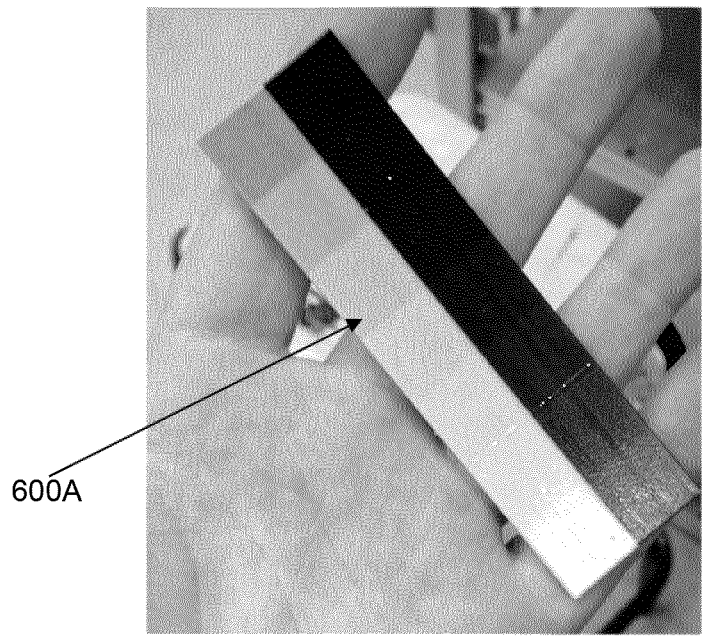
FIGS. 6A-6C depict articles according to exemplary embodiments.
Figure 6B:
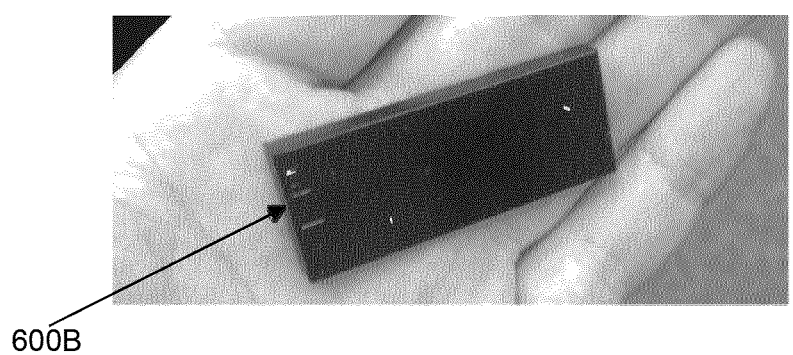
Figure 6C:
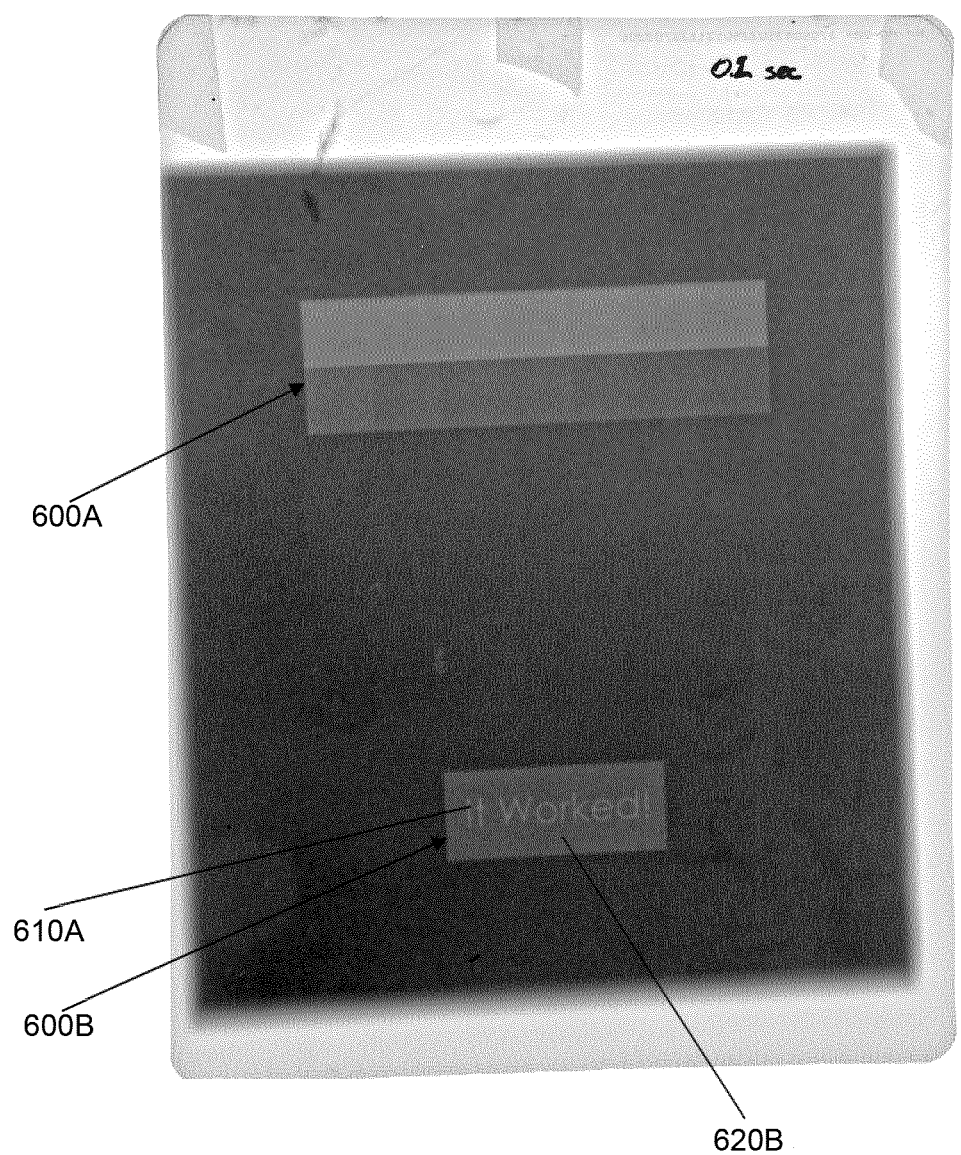

FIGS. 6A-6C depicts articles according to exemplary embodiments. Particularly, FIG. 6A shows a photograph of an article 600A according to an exemplary embodiment and FIG. 6B shows a photograph of an article 600B according to an exemplary embodiment. FIG. 6C shows a radiograph of the two articles 600A-600B, imaged as described with respect to FIG. 5C. From FIG. 6C, a first 3D printed region 610A having a first radiopacity of the article 600A is shown as a phrase 'It Worked!', in which letters of the phrase are formed from 1 mm thick OBJET VEROWHITEPLUS RGD835 including from 0.1 to 25 wt. % radiopaque particles comprising $ZrO_2$ centered inside 5 mm of Tangoplus rubber (i.e. a second 3D printed region 620B having a second radiopacity, wherein the first radiopacity is greater than the second radiopacity).

Figure 7A:
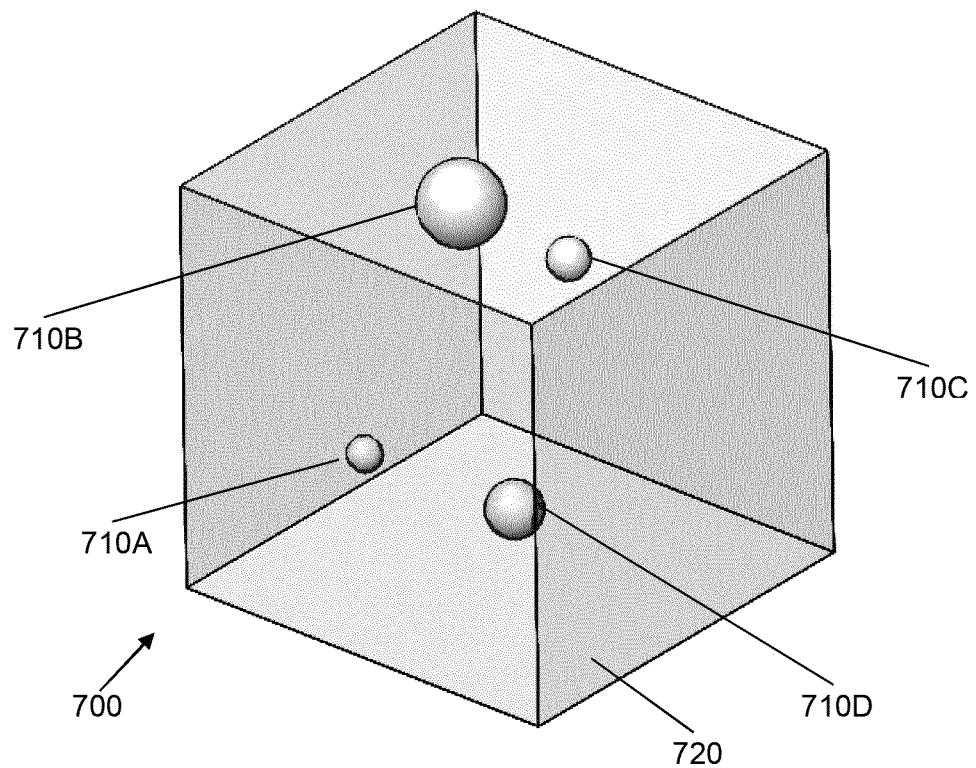
FIGS. 7A-7C schematically depict an article according to an exemplary embodiment.
Figure 7B:
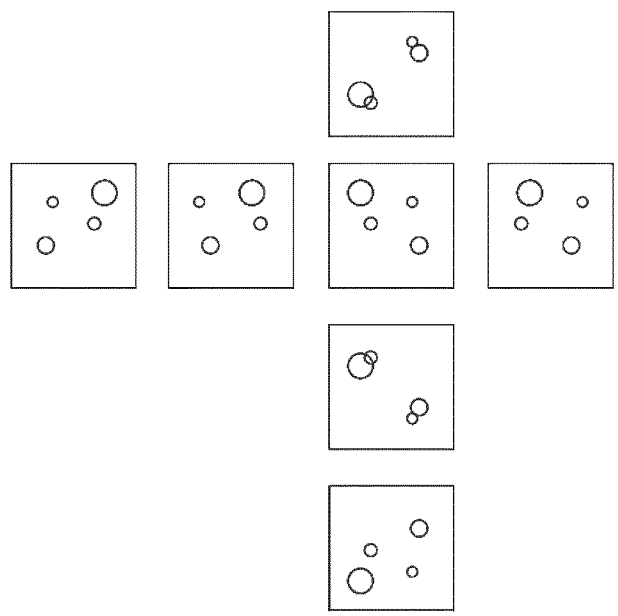
Figure 7C:
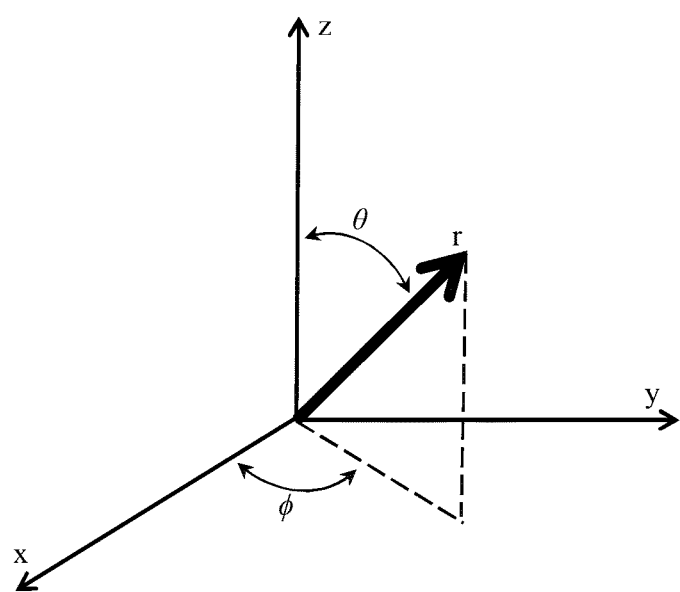

FIGS. 7A-7C schematically depict an article according to an exemplary embodiment. Particularly, FIG. 7A schematically depicts a projection view of an article 700 comprising four first 3D printed regions 710A-710D having a first radiopacity, 3D printed as spheres of different diameters, in a cube of a second 3D printed region 720 having a second radiopacity, wherein the first radiopacity is greater than the second radiopacity. FIG. 7B schematically depicts radiographs of the article 700 obtained from seven different angles. FIG. 7C depicts a coordinate system, for reference for the article 700 and as described below.

Particularly, the first 3D printed regions 710A-710D of the article 700 provide at least in part, comprise and/or is an identifier of the 3D printed article, as described in more detail below.

An extension of basic covert identification is the ability to create 3 dimensional, heavily encrypted, identifiers. These may be more suited to the aerospace or defence sector, for example, or any high value add products that are susceptible to counterfeiting. An example of such a high value add product is an oil filtration unit for a machine containing such an oil filtration unit. Defence of the filtration market is often of the form that use of a counterfeit replacement filtration unit may void the warranty of the machine. However, the filtration industry's problem is that they often cannot tell the difference between the original part and the counterfeit part. A detailed method of one embodiment 700 is provided by FIGS. 7A-7B.

In FIG. 7A, a cube 700 (of sides 15 mm) has four unequal spheres 710A-710D printed internally. The location of the spheres in the 3D space is generated by an algorithm, encrypting the identification data. A projection is shown of the cube under x-ray imaging from seven angles FIG. 7B, with each sphere appearing as a dot within a square. The positioning of the dots only aligns with the encryption "key" when viewed from the correct angle.

This method requires would-be forgers to have access to:
The original identifying codes.
The encryption keys.
The correct viewing angle.
The ability to 3D print radiopaque markers internally in a larger structure Detailed Method
1. Generate an appropriate encrypted serial number for the product, S.
2. Randomly choose a number of dots, n.
3. Randomly choose three coordinates for each of the n dots in polar coordinates $(r, \theta, \phi)_i$ where i=1, 2, 3, . . . , n and $0 \leq r \leq \infty$ and $0 \leq \theta \leq \pi$ and $0 \leq \phi \leq 2\pi$.
4. Randomly choose a size for each of the dots from, say, 3 sizes (small: z=1 mm, medium, z=3 mm, large, z=5 mm).
5. For a given product model, m, a scanning angle is chosen, $(\theta, \phi)_m$ which will remain unknown (this is an integral part of the encryption key).
6. Add the data: S, n, m, $(r, \theta, \phi)_i$, z and $(\theta, \phi)_m$ to a database.
7. Print the pattern, of dots embedded in the product in 3D.
8. Create a 2-D image of the dots by viewing the pattern along the direction $(\theta, \phi)_m$.
9. Add the image to the database and associate it with the serial number.

Unless the angle $(\theta, \phi)_m$ is known, it is not possible to know if you are viewing the correct pattern. The correct pattern could be viewed by an individual who takes a CT scan by 'getting lucky' and viewing along the correct angle but would not know it is the correct pattern.

The angle of view, the pattern and the associated serial number in the database are the 'key' to the overall encryption.

While the article 700 including the identifier described with reference to FIG. 7 may be formed by 3D printing using the flowable liquid formulation for 3D printing described herein, this is just one example of forming the identifier, which may be formed also using other formulations for 3D printing.

Figure 8:
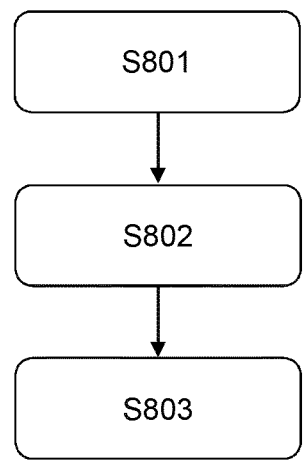
FIG. 8 schematically depicts a method of forming an article by 3D printing according to an exemplary embodiment.

FIG. 8 schematically depicts a method of forming an article by 3D printing according to an exemplary embodiment.

At S801, a first 3D printed region having a first radiopacity is printed from a first polymerizable formulation.

At S802, a second 3D printed region having a second radiopacity is printed from a second polymerizable formulation, wherein the first radiopacity is greater than the second radiopacity.

At S803, the first polymerizable formulation and the second polymerizable formulation are polymerized. The first formulation is as described previously.

Figure 9A:
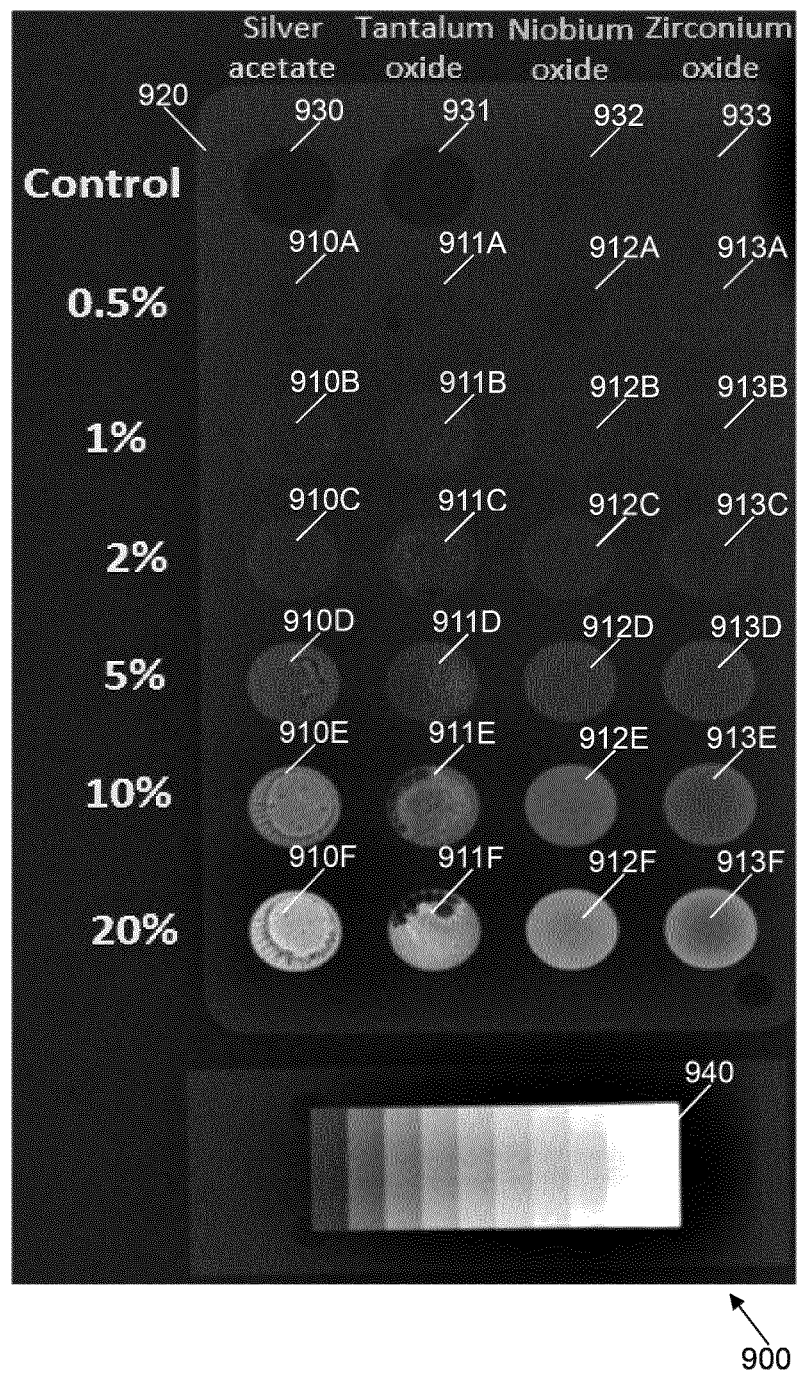
FIGS. 9A-9C depict an article according to an exemplary embodiment.
Figure 9B:
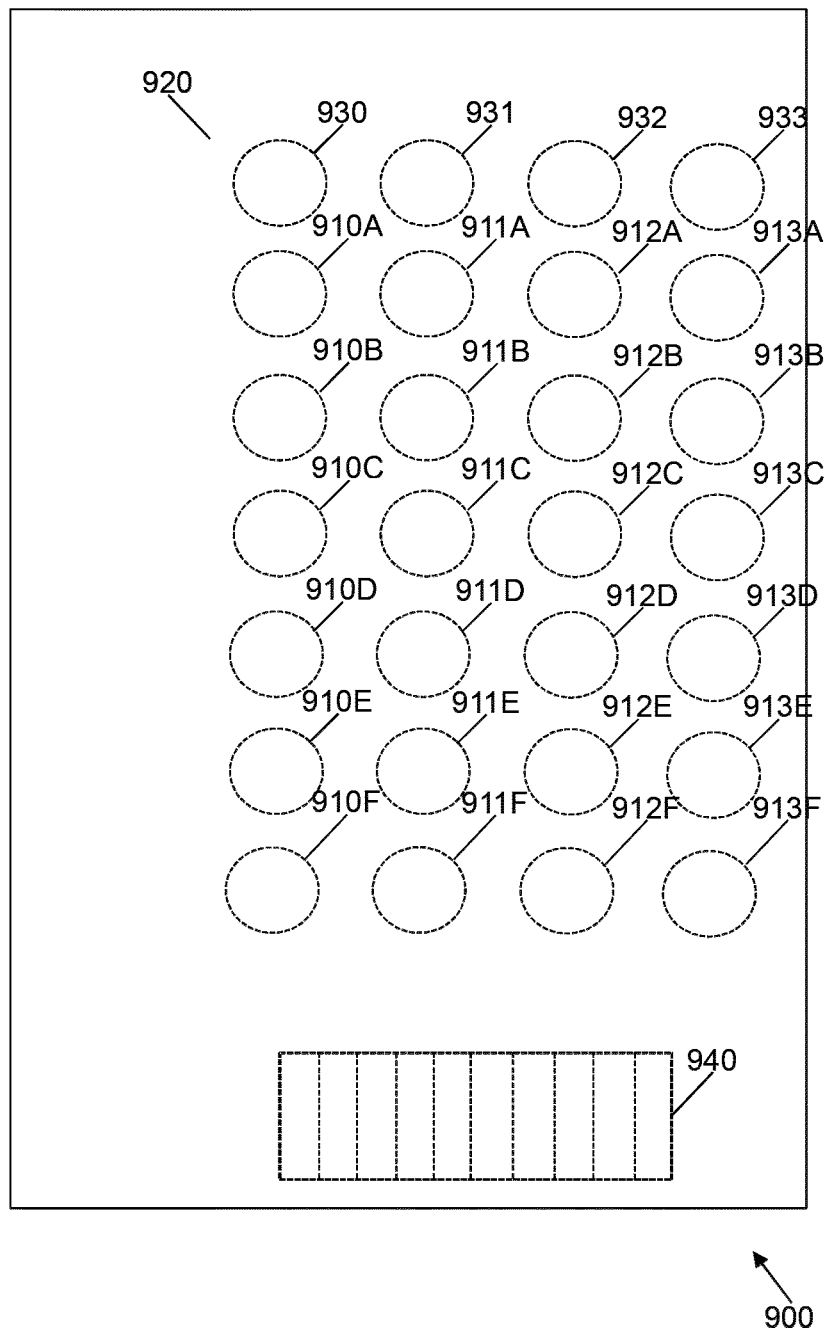
Figure 9C:
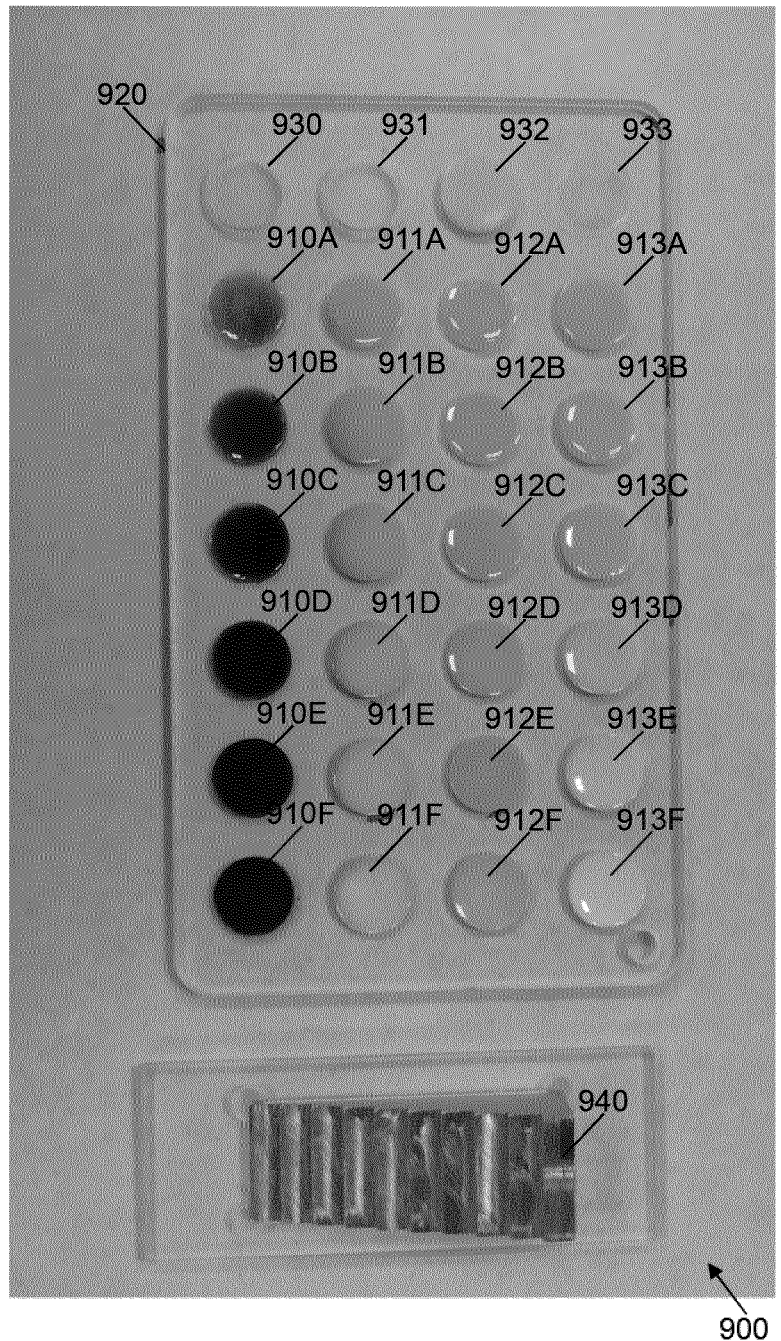

FIGS. 9A to 9C depict an article 900 according to an exemplary embodiment. Particularly, FIG. 9A depicts a radiograph of the article 900, FIG. 9B schematically depicts a corresponding plan view of the article 900 and FIG. 9C is an optical photograph of the article 900.

The article 900 is formed, at least in part, by 3D printing. The article 900 comprises a first 3D printed region 910 having a first radiopacity and a second region 920 having a second radiopacity, wherein the first radiopacity is greater than the second radiopacity. In this example, the second region 920 comprises a plate formed from Poly(methyl methacrylate) (PMMA, also known as acrylic), having 2 mm deep wells provided, by milling, therein. Correspondingly-shaped disks of first 3D printed regions 910 are arranged in the wells.

In more detail, the article 900 comprises six first 3D printed regions 910A-910F having different first radiopacities, increasing in the order from the first 3D printed region 910A to the first 3D printed region 910F. The article 900 comprises six first 3D printed regions 911A-911F, six first 3D printed regions 912A-912F and six first 3D printed regions 913A-913F. As described below in more detail, the six first 3D printed regions 910A-910F, the six first 3D printed regions 911A-911F, the six first 3D printed regions 912A-912F and the six first 3D printed regions 913A-913F comprise different materials. Similar to the first 3D printed region 110 of the article 100 described above, the six first 3D printed regions 910A-910F are cylindrical discs, internal to the article 900, completely surrounded by and/or embedded in the PMMA plate (grey region around disks only—not labelled). The six first 3D printed regions 910A-910E are arranged spaced apart in a regular array in the article 900. The six first 3D printed regions 911A-911F, the six first 3D printed regions 912A-912F and the six first 3D printed regions 913A-913F are generally as described with respect to the six first 3D printed regions 910A-910F, mutatis mutandis.

The article 900 further comprises control samples: 930 and 931 are unfilled wells, 932 is Verowhite RDG835 resin (no additives), 933 is VeroClear RDG810 resin (no additives). Control samples 930, 931,932, 933 are included in the PMMA plate as controls, and have similar dimensions to the 24 3D printed regions 910A-913F and similarly arranged. The control samples 930, 931, 932, 933 have a radiopacity of about 400 HU. The article 900 further comprises a conventional calibration standard 940 in the form of a step wedge according to ASTM F640 Standard Test Methods for Determining Radiopacity for Medical Use.

The six first 3D printed regions 910A-910F are formed by 3D printing using the 3D printer ink OBJET VEROClear RDG810 including from 0.5 to 20 wt. % radiopaque particles comprising silver acetate ($CH_3CO_2Ag$) particles, wherein at least 50% of the silver acetate particles have a diameter of at most 100 nm (i.e. a flowable liquid formulation for 3D printing, a second polymerizable formulation). Silver acetate particles are available from Sigma Aldrich as 216674 and were milled to nanopowder scale (i.e. wherein at least 50% of the silver acetate particles have a diameter of at most 100 nm).

The six first 3D printed regions 910A-910F are formed by 3D printing the flowable liquid formulation comprising different amounts of the silver acetate particles, thereby providing different first radiopacities, specifically 0.5 wt. %, 1 wt. %, 2 wt. %, 5 wt. %, 10 wt. % and 20 wt. % respectively.

The six first 3D printed regions 911A-911F are formed by 3D printing using the 3D printer ink OBJET VEROClear RDG810 including from 0.5 to 20 wt. % radiopaque particles comprising $Ta_2O_5$ particles, wherein at least 50% of the $Ta_2O_5$ particles have a diameter of at most 100 nm (i.e. a flowable liquid formulation for 3D printing, a second polymerizable formulation). $Ta_2O_5$ particles are available from Sigma Aldrich as 204536 and were milled to nanopowder scale (i.e. wherein at least 50% of the $Ta_2O_5$ particles have a diameter of at most 100 nm).

The six first 3D printed regions 911A-911F are formed by 3D printing the flowable liquid formulation comprising different amounts of the $Ta_2O_5$ particles, thereby providing different first radiopacities, specifically 0.5 wt. %, 1 wt. %, 2 wt. %, 5 wt. %, 10 wt. % and 20 wt. % respectively.

The six first 3D printed regions 912A-912F are formed by 3D printing using the 3D printer ink OBJET VEROClear RDG810 including from 0.5 to 20 wt. % radiopaque particles comprising $Nb_2O_5$ particles, wherein at least 50% of the $Nb_2O_5$ particles have a diameter of at most 100 nm (i.e. a flowable liquid formulation for 3D printing, a second polymerizable formulation). $Nb_2O_5$ particles are available from Sigma Aldrich as 203920 and were milled to nanopowder scale (i.e. wherein at least 50% of the $Nb_2O_5$ particles have a diameter of at most 100 nm).

The six first 3D printed regions 912A-912F are formed by 3D printing the flowable liquid formulation comprising different amounts of the $Nb_2O_5$ particles, thereby providing different first radiopacities, specifically 0.5 wt. %, 1 wt. %, 2 wt. %, 5 wt. %, 10 wt. % and 20 wt. % respectively.

The six first 3D printed regions 913A-913F are formed by 3D printing using the 3D printer ink OBJET VEROClear RDG810 including from 0.5 to 20 wt. % radiopaque particles comprising $ZrO_2$ particles, wherein at least 50% of the $ZrO_2$ particles have a diameter of at most 100 nm (i.e. a flowable liquid formulation for 3D printing, a second polymerizable formulation). The $ZrO_2$ particles are available from Sigma Aldrich as 544760 Aldrich Zirconium(IV) oxide nanopowder <100 nm particle size (as determined by TEM).

The six first 3D printed regions 913A-913F are formed by 3D printing the flowable liquid formulation comprising different amounts of the $ZrO_2$ particles, thereby providing different first radiopacities, specifically 0.5 wt. %, 1 wt. %, 2 wt. %, 5 wt. %, 10 wt. % and 20 wt. % respectively.

Particularly, radiopacities of the various regions increase in an order the control sample 932,933, the first 3D printed region 910A, the first 3D printed region 910B, the first 3D printed region 910C, the first 3D printed region 910E and the first 3D printed region 910F. Radiopacities of the first 3D printed region 911A-911F, 912A-912F and 913A-913F increase similarly to the first 3D printed region 910A-910F.

Furthermore, for a given amount of the particles, the radiopacities of the various regions increase in an order $ZrO_2$, $Nb_2O_5$, $Ta_2O_5$ and silver acetate, In this way, the article 900 may provide a calibration standard for a medical radiography apparatus by comprising the thirty first 3D printed regions 910A-913F formed by 3D printing.

Although a preferred embodiment has been shown and described, it will be appreciated by those skilled in the art that various changes and modifications might be made without departing from the scope of the invention, as defined in the appended claims and as described above.

In summary, the invention provides a flowable liquid formulation for 3D printing, an article formed by 3D printing, a method of forming an article by 3D printing, and use of a flowable liquid formulation comprising from 0.1 to 25 wt. % radiopaque particles. In this way, articles having regions of desired radiopacity may be formed by 3D printing, for example.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. A flowable liquid formulation for 3D printing a solidified article having a radiopacity of at least 200 HU up to 1200 HU, the flowable liquid formulation comprising:
   from 0.1 to 25 wt. % radiopaque particles, wherein at least 50% of the particles have a diameter of at most 100 nm; and
   monomeric, oligomeric and/or polymeric precursors adapted for polymerization to form the solidified article;
   wherein the flowable liquid formulation comprises from 5 to 80 wt. % oligomeric precursors; and
   wherein the dynamic viscosity, measured at 20° C., of the flowable liquid formulation is in a range from 100 to 1000 centipoise.

2. The flowable liquid formulation according to claim 1 comprising from 5 to 10 wt. % radiopaque particle.

3. The flowable liquid formulation according to claim 1 wherein the radiopaque particles comprise $ZrO_2$ particles, $Nb_2O_5$ particles, $Ta_2O_5$ particles and/or silver acetate ($CH_3CO_2Ag$) particles.

4. The flowable liquid formulation according to claim 1 comprising from 40 to 80 wt. % monomeric, oligomeric and/or polymeric precursors.

5. The flowable liquid formulation according to claim 1 comprising from 20 to 60 wt. % monomeric precursors.

6. The flowable liquid formulation according to claim 1 comprising at least one of a photoinitiator, a retarder solvent, a filler and a colouring agent.

7. An article formed by 3D printing, the article having a radiopacity of at least 200 HU up to 1200 HU, the article comprising a first 3D printed region having a first radiopacity and a second 3D printed region having a second radiopacity, wherein the first radiopacity is greater than the second radiopacity, wherein the first 3D printed region is obtained by polymerisation of the formulation according to claim 1.

8. The article according to claim 7, wherein the artic a calibration standard for a medical radiography apparatus.

9. The article according to claim 7, wherein the article is a medical device.

* * * * *